US009492547B2

(12) United States Patent
Cooper et al.

(10) Patent No.: US 9,492,547 B2
(45) Date of Patent: Nov. 15, 2016

(54) POLYMORPHIC FORM OF INULIN AND USES THEREOF

(75) Inventors: Peter D. Cooper, Monash (AU); Nikolai Petrovsky, Forrest (AU)

(73) Assignee: VAXINE PTY LTD, Adelaide (AU)

( * ) Notice: Subject to any disclaimer, the term of this patent is extended or adjusted under 35 U.S.C. 154(b) by 2297 days.

(21) Appl. No.: 11/661,667

(22) PCT Filed: Sep. 1, 2005

(86) PCT No.: PCT/AU2005/001328
§ 371 (c)(1),
(2), (4) Date: Apr. 11, 2008

(87) PCT Pub. No.: WO2006/024100
PCT Pub. Date: Mar. 9, 2006

(65) Prior Publication Data
US 2009/0029940 A1    Jan. 29, 2009

(30) Foreign Application Priority Data

Sep. 2, 2004    (AU) ................................ 2004905032

(51) Int. Cl.
*A61K 31/733*    (2006.01)
*A61K 47/36*    (2006.01)
*C08B 37/00*    (2006.01)

(52) U.S. Cl.
CPC ............. *A61K 47/36* (2013.01); *A61K 31/733* (2013.01); *C08B 37/0054* (2013.01)

(58) Field of Classification Search
CPC .................................................... A61K 31/733
USPC ............................ 514/54, 885; 536/127, 123
See application file for complete search history.

(56) References Cited

U.S. PATENT DOCUMENTS

| 4,954,622 | A | * | 9/1990 | Cooper | ........................ 536/127 |
| 5,051,408 | A | | 9/1991 | Cooper | |
| 5,422,346 | A | | 6/1995 | Mitchell et al. | |
| 5,476,844 | A | * | 12/1995 | Cooper | ........................ 514/55 |
| 5,840,884 | A | | 11/1998 | Lis et al. | |
| 6,303,778 | B1 | * | 10/2001 | Smits et al. | ................. 536/128 |

FOREIGN PATENT DOCUMENTS

WO    WO 87/02679 A1    5/1987
WO    WO 90/01949 A1    3/1990

OTHER PUBLICATIONS

Andre, I. et al., "Single Crystals of Inulin," International Journal of Biological Macromolecules, 1996, pp. 195-204, vol. 18.
Cooper, P.D. et al., "Algammulin, a New Vaccine Adjuvant Comprising Gamma Inulin Particles Containing Alum: Preparation and In Vitro Properties," Vaccine, May 1991, pp. 351-357, vol. 9.
Cooper, P.D. et al., "Anti-Complementary Action of Polymorphic "Solubility Forms" of Particulate Inulin," Molecular Immunology, 1996, pp. 895-901, vol. 23, No. 8.
European Supplementary Search Report, European Application No. 05775959.9, Aug. 10, 2011, 7 pages.
Hebette, C.L.M. et al., "Complex Melting of Semi-Crystalline Chicory (*Cichorium intybus* L.) Root Inulin," Carbohydrate Research, 1998, pp. 65-75, vol. 310.
PCT International Search Report, PCT Application No. PCT/AU2005/001328, Oct. 11, 2005, 3 pages.
PCT International Preliminary Report on Patentability, PCT Application No. PCT/AU2005/001328, Jul. 27, 2006, 7 pages.
STN Medline, PubMed ID: 1872020: Cooper, P.D. et al., "Algammulin, a New Vaccine Adjuvant Comprising Gamma Inulin Particles Containing Alum: Preparation and in Vitro Properties," Vaccine, May 1991,pp. 351-357, vol. 9, No. 5.
STN Medline, PubMed ID: 3540619: Cooper, P.D. et al., "The Anti-Melanoma Activity of Inulin in Mice," Molecular Immunology, Aug. 1986, pp. 903-908, vol. 23, No. 8.
STN Medline, PubMed ID 3796631: Cooper, P.D. et al., "Anti-Complementary Action of Polymorphic "Solubility Forms" of Particulate Inulin," Molecular Immunology, Aug. 1986, pp. 895-901, vol. 23, No. 8.
STN Medline, PubMed ID 3265692: Cooper, P.D. et al., "The Adjuvanticity of Gamma Inulin," Immunology and Cell Biology, Oct.-Dec. 1988, pp. 345-352, vol. 66, No. 5-6.
STN File CA, Abstract 26:22717: Katz, J.R. et al., "Polymorphism of Substances of High Molecular Weight. IL. Amorphous and Crystalline Inulin," Recueil des Travaux Chimiques des Pays-Bas et de la Belgique, 1931, pp. 1133-1137, vol. 50.

* cited by examiner

*Primary Examiner* — Patrick Lewis
*Assistant Examiner* — Everett White

(57) ABSTRACT

The present invention relates to a new polymorphic form of inulin, designated delta inulin (dIN), to methods for the preparation of dIN, compositions comprising dIN and uses thereof. The present invention also relates to the use of dIN and compositions comprising dIN in the preparation of gamma inulin (gIN), compositions comprising gIN and uses thereof.

29 Claims, 14 Drawing Sheets

POLYMORPHIC FORM OF INULIN AND USES THEREOF

CROSS-REFERENCE TO RELATED APPLICATIONS

This application is the National Stage of International Application No. PCT/AU2005/001328, filed 1 Sep. 2005, which claims the benefit of Australian Application No. 2004905032, filed 2 Sep. 2004, the disclosures of which are incorporated herein by reference in their entirety.

TECHNICAL FIELD

The present invention relates to a new polymorphic form of inulin, designated delta inulin (dIN), to methods for the preparation of dIN, compositions comprising dIN and uses thereof. The present invention also relates to the use of dIN and compositions comprising dIN in the preparation of gamma inulin (gIN), compositions comprising gIN and uses thereof.

BACKGROUND ART

Inulin is a simple, inert polysaccharide comprising a family of linear β-D-(2→1) polyfructofuranosyl α-D-glucoses, in which an unbranched chain of up to 100 fructose moieties or more is linked to a single terminal glucose, the end fructose-glucose pair incidentally being identical to sucrose. Inulin preparations therefore comprise neutral polysaccharides of simple, known composition, but which are molecularly polydisperse, with molecular weights ranging up to 16,000 or beyond. Inulin is the storage carbohydrate of Compositae and is cheaply available from dahlia tubers. It has a relatively hydrophobic, polyoxyethylene-like backbone, and this unusual structure plus its non-ionised nature allows recrystallisation and easy preparation in a very pure state.

Although the molecular composition of inulin is well known, the reported determinations of its solubility are conflicting. For example, the Merck Index (Thirteen Edition, 2001) describes inulin as "slightly soluble in cold water and organic solvents, soluble in hot", whereas a quantitative study (Phelps, C. F., (1965) *Biochem. J*, 95:41-47) suggested that two distinct forms of inulin exist—the first obtained by precipitation from water, the second by precipitation from ethanol—both of which are substantially soluble in water at 37° C. It is also known that suspensions of inulin become less soluble on standing. The form obtained by precipitation from water is referred to as alpha-inulin (aIN), and the form obtained by precipitation from ethanol is known as beta inulin (bIN).

A third polymorphic form of particulate inulin, designated gamma inulin (gIN), is disclosed in U.S. Pat. Nos. 4,954,622 and 5,051,408, the contents of which are incorporated herein by reference. See also Cooper, P. D. and Carter, M., (1986) *Molec. Immunol.* 23(8):895-901, and Cooper, P. D. and Steele, E. J., (1988) *Immunol. Cell Biol.* 66:345-352.

This third polymorphic form is virtually insoluble in water at 37° C., but is soluble in concentrated solution (for example 50 mg/ml) only at temperatures in the range of 70° C.—80° C., as are the alpha and beta forms. This series of three polymorphic forms in which inulin crystallises may be characterised by their different solubility rates in aqueous media ranging from one instantly soluble at 23° C. (beta$_{23}^0$ inulin) through a form soluble at 37° C. with a half-time of 8 minutes (alpha$_{37}^8$ inulin) to a form virtually insoluble at 37° C. (gamma inulin). All forms are interconvertible, the more soluble and unstable progressing on standing to less soluble and more stable forms, only reversible by complete solution followed by recrystallisation, with the end product being the stable gIN.

Subsequently, it was disclosed that the activity of the gamma polymorphic form of inulin as an immunoactive agent, particularly an adjuvant, could be enhanced if particles of gIN were associated with an antigen-binding carrier material, and that this association provides synergistic effects. Thus, particles can be formed by association of gIN with aluminium hydroxide (alum) gel to form a gIN/alum hybrid preparation referred to as "Algammulin"—see also U.S. Pat. No. 5,476,844, the contents of which are incorporated herein by reference, and Cooper, P. D. and Steele, E. J., (1991) *Vaccine* 9:351-357.

Notwithstanding the preference stated in the above US patents for particles <1 μm in diameter, more recent and more accurate determinations of the size of the particles in the inulin preparations described in those earlier patents has revealed that, when measured in hydrated form, the finest of these earlier preparations turned out to have only a minority of particles <1 μm in diameter. This is the case even after treatment with an ultrasonic disruption device as described in U.S. Pat. No. 5,476,844.

However, the preparation of gIN and gIN/alum hybrid (Algammulin) by use of dIN in accordance with the present invention does result in ultra-fine formulations in which at least a majority of the particles have a diameter of <1 μm, as shown in the examples below. Thus the present invention achieves a particle size that the earlier patents set out, unsuccessfully, to achieve.

The ability to produce fine or ultrafine particles of inulin of less than 1 μm in diameter has therapeutic significance, with such particles being useful for example as adjuvants. In particular, the preparation of such particles is important in enhancing their biological activity and in reducing undesirable side effects such as local reactogenicity when the particles are used in human or non-human animal patients.

The present invention is therefore predicated on the serendipitous twofold observations of the very small but consistent residual turbidity after attempts to dissolve gIN particles above 50° C., resulting in the discovery of a novel polymorphic form of particulate inulin designated dIN, and the anomalous appearance and behaviour of these particles near their temperature of complete dissolution, resulting in the novel concept of fragmentation of such particles to form micronuclei for recrystallisation in fine or ultra-fine particulate form.

The reference to any prior art in this specification is not, and should not be taken as, an acknowledgment or any form of suggestion that that prior art forms part of the common general knowledge in Australia.

SUMMARY OF THE INVENTION

According to a first aspect of the present invention there is provided inulin in a delta polymorphic form.

The inulin in a delta polymorphic form may comprise a particulate form. The particulate form may comprise a majority of particles having a diameter less than 1 μm. The diameter may be in a range of from about 50 nm to 600 nm.

The inulin in a delta polymorphic form may have a 50% OD$_{700}$ thermal transition point in dilute suspensions greater than 50° C. The inulin in a delta polymorphic form may have a 50% OD$_{700}$ thermal transition point in dilute suspensions in a range of from about 53° C. to 58° C.

The inulin in a delta polymorphic form may have a molecular weight in a range of from about 8,000 to 16,000 kD.

The inulin in a delta polymorphic form may have a low rate of solution in aqueous media above 37° C. The inulin in a delta polymorphic form may have a low rate of solution in aqueous media above 40° C. The inulin in a delta polymorphic form may have a low rate of solution in aqueous media above 50° C.

According to a second aspect of the present invention there is provided an immunological composition comprising the inulin of the first aspect together with a pharmaceutically acceptable carrier, diluent or excipient.

According to a third aspect of the present invention there is provided an immunological composition comprising the inulin of the first aspect together with an antigen-binding carrier material. The antigen-binding carrier material may comprise at least one of aluminium hydroxide gel, calcium phosphate gel or aluminium phosphate gel.

According to a fourth aspect of the present invention there is provided a method for the preparation of delta inulin, wherein said method comprises heating a suspension comprising gamma-inulin at a temperature of about 50° C. or higher for a time of about up to 10 hours.

The method may comprise heating the suspension comprising gamma-inulin at a temperature of about 55° C. or higher for a time in a range of from about 90 minutes to 3 hours.

The method may further comprise heating the suspension comprising gamma-inulin at a temperature in a range of from about 60° C. to 70° C. for a time of up to about 1 hour. The time may be in a range of from about 5 minutes to 30 minutes.

The suspension may further comprise a pharmaceutically acceptable carrier, diluent or excipient.

Additionally or alternatively, the suspension may further comprise an antigen-binding carrier material. The antigen-binding carrier material may comprise at least one of aluminium hydroxide gel, calcium phosphate gel or aluminium phosphate gel.

According to a fifth aspect of the present invention there is provided the delta inulin prepared in accordance with the method of the fourth aspect.

According to a sixth aspect of the present invention there is provided a method for the preparation of gamma inulin, wherein said method comprises:
 (a) preparing a suspension of particles of inulin in a delta polymorphic form;
 (b) optionally fragmenting said particles in said suspension;
 (c) recrystallising inulin from said suspension;
 (d) converting said recrystallised inulin to a gamma polymorphic form; and
 (e) isolating said gamma-inulin in fine or ultrafine particulate form.

The optional fragmentation of the suspension in step (b) may comprise either the application of shear stress or ultrasonication while applying a temperature in a range of from about 60° C. to 72° C.

The recrystallisation of the suspension in step (c) may comprise applying a temperature of about 5° C.

The conversion in step (d) may comprise applying a temperature of about 45° C. for a time of about 45 minutes.

The method may further comprise:
 (f) converting said isolated gamma inulin in fine or ultrafine particulate form to delta inulin in fine or ultrafine particulate form.

The delta inulin may be converted from gamma inulin by heating a suspension comprising gamma-inulin at a temperature of about 50° C. or higher for a time of about up to 10 hours.

The delta inulin may be converted from gamma inulin by heating a suspension comprising gamma-inulin at a temperature of about 55° C. or higher for a time in a range of from about 90 minutes to 3 hours.

The prepared inulin may comprise a majority of particles with a diameter less than 1 μm. The diameter may be in a range of from about 50 nm to 600 nm.

According to a seventh aspect of the present invention there is provided the gamma inulin prepared in accordance with the method of the sixth aspect.

According to an eighth aspect of the present invention there is provided the delta inulin prepared in accordance with step (f) of the sixth aspect.

According to a ninth aspect of the present invention there is provided an immunological composition comprising the delta inulin according to the fifth aspect, the gamma inulin according to the seventh aspect or the delta inulin according to the eighth aspect together with a pharmaceutically acceptable carrier, diluent or excipient.

According to a tenth aspect of the present invention there is provided an immunological composition comprising the delta inulin according to the fifth aspect, the gamma inulin according to the seventh aspect or the delta inulin according to the eighth aspect together with an antigen-binding carrier material. The antigen-binding carrier material may comprise at least one of aluminium hydroxide gel, calcium phosphate gel or aluminium phosphate gel.

According to an eleventh aspect of the present invention there is provided a method for stimulating an immune response, wherein said method comprises administering to a subject a therapeutically effective amount of an immunotherapeutic agent comprising:
 (a) the inulin according to any one of the first, fifth, seventh or eighth aspects; or
 (b) the immunological composition according to any one of the second, third, ninth or tenth aspects.

The immune response may comprise activation of the alternative pathway of complement.

According to a twelfth aspect of the present invention there is provided a method for enhancing an immune response, wherein said method comprises administering to a subject a therapeutically effective amount of an adjuvant, wherein said adjuvant comprises:
 (a) the inulin according to any one of the first, fifth, seventh or eighth aspects; or
 (b) the immunological composition according to any one of the second, third, ninth or tenth aspects.

According to a thirteenth aspect, of the present invention there is provided a method for treating cancer, wherein said method comprises administering to a subject a therapeutically cally effective amount of:
 (a) the inulin according to any one of the first, fifth, seventh or eighth aspects; or
 (b) the immunological composition according to any one of the second, third, ninth or tenth aspects.

DEFINITIONS

Figure 1:
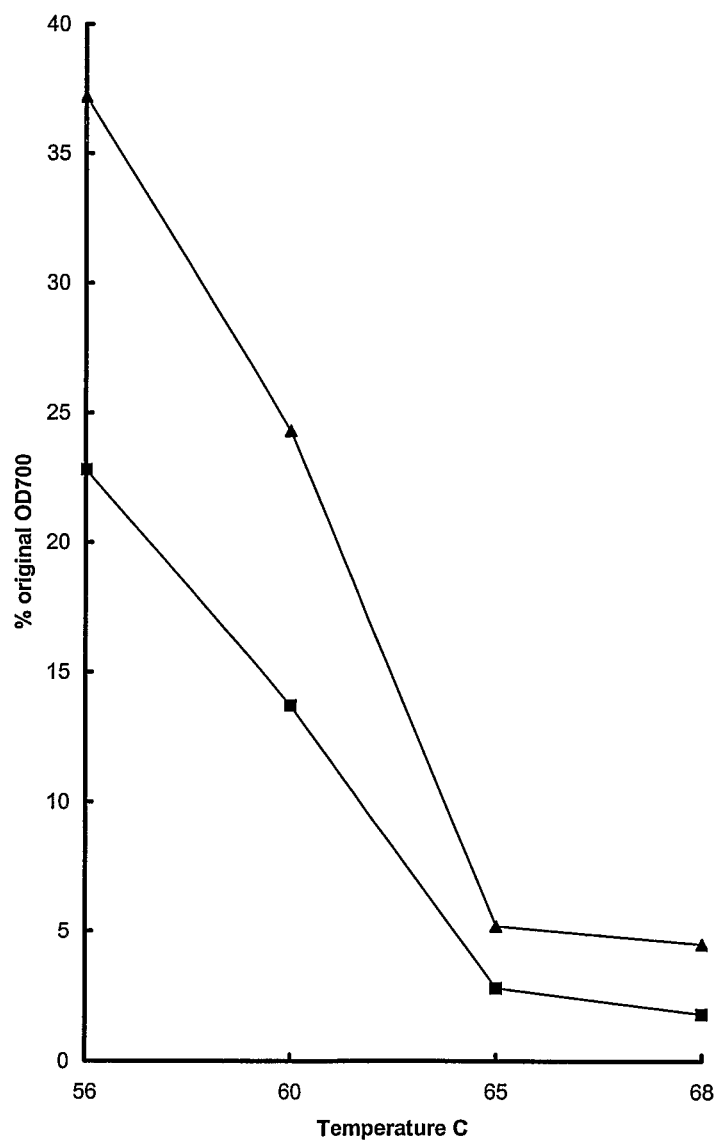
FIG. 1 shows the decay in dIN content with increase in temperature in an ultra-fine formulation of gIN (gIN-0495, upper curve) and an ultra-fine formulation of Algammulin (AG-38ff, lower curve). The preparations (50 mg/ml) were heated for 30 min at 56° C., when the dIN content (in terms of $OD_{700}$ of a 2 mg/ml dilution after heating for 10 min at 50° C.) had increased from 6.4% to 37.2% and 3.0% to 22.8%, respectively. 1 ml samples (50 mg/ml) were then heated for 5 min at the indicated temperatures, after which 0.2 ml samples were diluted in 4.8 ml PBS for $OD_{700}$ assay after a further 10 min at 50° C.

As used herein, the term "comprising" means "including principally, but not necessarily solely". Furthermore, variations of the word "comprising", such as "comprise" and "comprises", have correspondingly varied meanings.

As used herein the terms "treating" and "treatment" refer to any and all uses which remedy a condition or symptoms, prevent the establishment of a condition or disease, or otherwise prevent, hinder, retard, or reverse the progression of a condition or disease or other undesirable symptoms in any way whatsoever.

As used herein the term "effective amount" includes within its meaning a non-toxic but sufficient amount of an agent or compound to provide the desired effect. The exact amount required will vary from subject to subject depending on factors such as the species being treated, the age and general condition of the subject, the severity of the condition being treated, the particular agent being administered and the mode of administration and so forth. Thus, it is not possible to specify an exact "effective amount". However, for any given case, an appropriate "effective amount" may be determined by one of ordinary skill in the art using only routine experimentation.

As used herein, the term "inulin" is to be understood to include not only inulin, β-D-[2-1]-polyfructofuranosyl α-D-Glucose, but also derivatives thereof including β-D-[2-1] polyfructose which may be obtained by enzymatic removal of the end glucose from inulin, for example using an invertase or inulase enzyme capable of removing this end glucose. Other derivatives included within the ambit of this term are derivatives of inulin in which the free hydroxyl groups have been etherified or esterified, for example by chemical substitution with alkyl, aryl or acyl groups by known methods.

BEST MODE OF PERFORMING THE INVENTION

In work leading to the present invention, a new polymorphic form of inulin, termed delta inulin (dIN), has been identified and defined. Furthermore, a new method of recrystallisation involving dIN has been developed to create gIN and compositions comprising gIN (such as Algammulin) in particles much smaller than those obtained by earlier methods of preparation. The preparation of these smaller particles is particularly important in enhancing their biological activity and in reducing undesirable side effects such as local reactogenicity when the particles are used in human or non-human animal patients.

The physico-chemical properties of particulate inulin, and in particular its transformations among various polymorphic forms and their solubility in water at different temperatures are characterised by relatively large physical changes over quite small temperature ranges, sometimes less than 5° C. (Cooper and Carter, 1986; Cooper and Steele, 1991). Examples of this are the changes from the several beta inulins to the different polymorphic forms termed alpha inulins on standing at temperatures below 30° C., the shift to gIN that develops between 35° C. and 45° C., and the sharp increases in solubility over a 2-3° C. range, resembling in abruptness a melting point, with increase in temperature. This is especially marked with gIN, one definition of which may be inulin having a 50% $OD_{700}$ thermal transition point in dilute suspension of 48±1° C.

Similar characteristics are seen again in the formation and properties of delta inulin (dIN), which is a fourth polymorphic form of particulate inulin, adding to the three previously described alpha, beta and gamma forms. dIN may be defined as having a 50% $OD_{700}$ thermal transition point in dilute suspension of 54-58° C., and is clearly distinguished from that of gIN. It is optimally formed in concentrated suspension above 50° C., again in clear contrast to gIN whose formation above 45° C. greatly decreases in favour of an increase in dIN. It appears to comprise the residual skeleton or framework of inulin particles that is still present at temperatures close to those giving complete solution.

It can be observed in the haemocytometer that when suspensions of gIN particles or of derivative compositions (eg Algammulin) are progressively heated close to the temperature of complete solution (60-70° C.), the dissolving particles do not become smaller but become rather larger and much fainter ("ghosts"). These full-sized 'ghosts' finally break up into smaller fragments before becoming invisible in the haemocytometer at above 65° C. The ghosts are in fact made up almost entirely of dIN, as shown in the following Examples.

These ghost fragments may serve as multiple micronuclei for subsequent recrystallisation. Since each ghost yields many fragments, the resulting more numerous particles obtained from the same total amount of inulin should be smaller in mass than the original. This turned out to be the case, as shown in the Examples. It is preferable to ensure that the prior content of dIN is sufficiently high, and the samples are desirably pre-heated at 55° C. for long enough to obtain the optimum content of dIN.

Accordingly, the present invention provides inulin in a delta polymorphic form. The inulin in a delta polymorphic form may comprise a particulate form. The particulate form may comprise a majority of particles having a diameter less than 1 μm. The diameter may be in a range of from about 50 nm to 600 nm.

The inulin in a delta polymorphic form may have a 50% $OD_{700}$ thermal transition point in dilute suspensions greater than 50° C. The inulin in a delta polymorphic form may have a 50% $OD_{700}$ thermal transition point in dilute suspensions in a range of from about 53° C. to 58° C.

Typically, the dIN has a molecular weight greater than about 3,000. More typically, the dIN has a molecular weight greater than about 8,000. Even more typically, the dIN has a molecular weight in the range of from about 8,000 to about 16,000.

Figure 3:
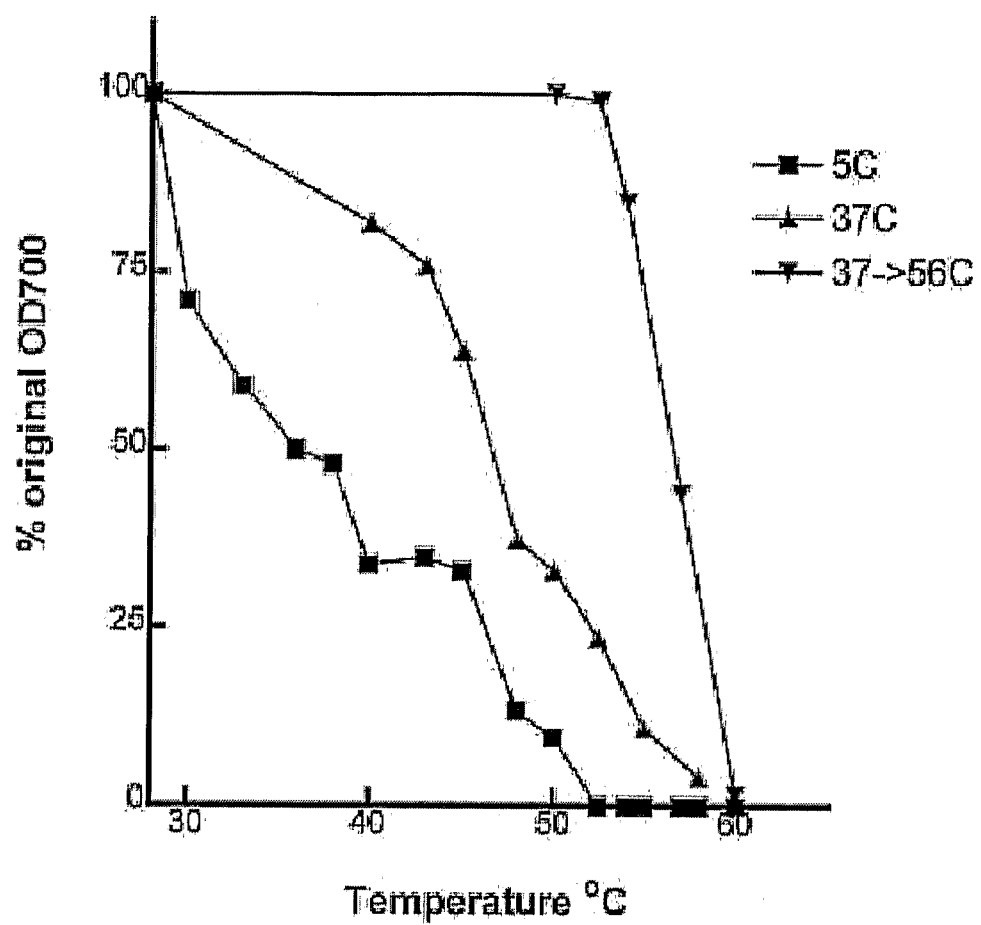
FIG. 3 shows results obtained when samples of 50 μl of the three inulin preparations as shown (dIN ghosts dissolved then recrystallised either at 5° C., or at 37° C. or at 37° C. then heated at 56° C., respectively) were diluted into 5 ml PBS and progressively heated in a water bath to the indicated temperatures, at which point their optical densities were measured.
Figure 10:
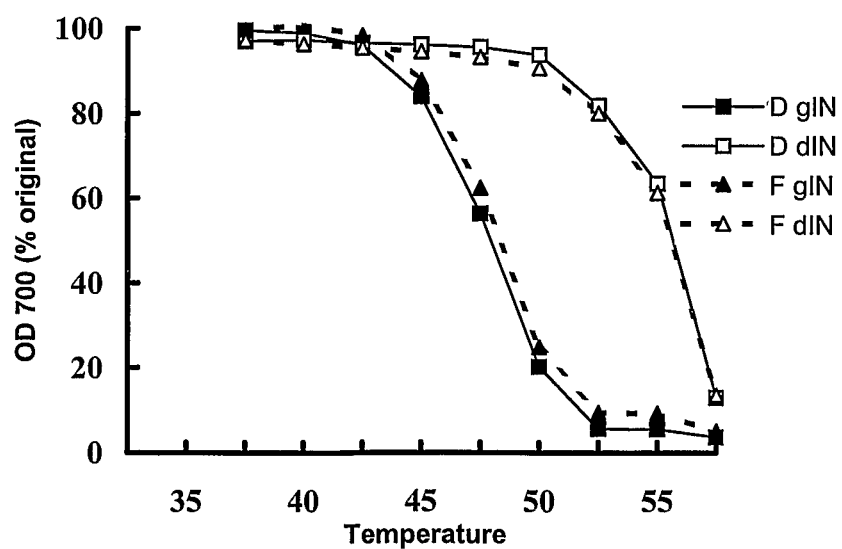
FIG. 10 shows results obtained when 50 μl of four of the ten samples described in Table 2 (CT2D ultra-fine, gIN and dIN forms, and CT2F ultra-fine, gIN and dIN forms) were diluted in 5 ml PBS and progressively heated in a water bath to the indicated temperatures, at which point their optical densities were measured.

The inulin in both gamma and delta polymorphic forms may have a low rate of solution in aqueous media at 37° C. (FIGS. 3 and 10). The inulin in a delta polymorphic form may have a low rate of solution in aqueous media above 40° C., while gIN may have an increasing rate (FIGS. 3 and 10). The inulin in a delta polymorphic form may have a low rate of solution in aqueous media above 50° C., while gamma inulin may have a high rate (FIGS. 3 and 10).

The present invention additionally provides for immunological compositions comprising the inulin in a delta polymorphic form as described above together with a pharmaceutically acceptable carrier, diluent or excipient.

The present invention further provides immunological compositions comprising the inulin in a delta polymorphic form as described above together with an antigen-binding carrier material. The antigen-binding carrier material may comprise any material of low solubility capable of binding proteinaceous, lipid, carbohydrate and/or other antigens. For example, the antigen-binding carrier material may be selected from metal-containing precipitates such as magnesium, calcium or aluminium phosphates, sulphates, hydroxides or hydrates thereof, organic bases such as chitin (poly N-acetylglucosamine) or deacetylated derivatives thereof or basic cellulose derivatives, or organic acids including sulphated or phosphorylated polysaccharides such as heparin, dextran or cellulose derivatives. The antigen-binding carrier material may comprise poorly soluble particles of such materials as aluminium hydroxide (alum) gel or a hydrated salt complex thereof. Typically, particles of the antigen-binding carrier material may be smaller than 1 μm in diameter. More typically, the particles may be 50-2000 nm in diameter. The antigen-binding carrier material is typically endotoxin-free and pyrogen-free, and pharmaceutically acceptable. Typically, the antigen-binding carrier material does not tend to aggregate or is treated to avoid aggregation. Most preferably, the antigen-binding carrier material may comprise at least one of aluminium hydroxide gel, calcium phosphate gel or aluminium phosphate gel.

The present invention also provides for methods for the preparation of delta inulin, wherein said method comprises heating a suspension comprising gamma-inulin at a temperature of about 50° C. or higher for a time of about up to 10 hours. The methods may comprise heating the suspension comprising gamma-inulin at a temperature of about 55° C. or higher for a time in a range of from about 90 minutes to 3 hours.

The suspension may further comprise a pharmaceutically acceptable carrier, diluent or excipient. Additionally or alternatively, the suspension may further comprise an antigen-binding carrier material. The antigen-binding carrier material may comprise at least one of aluminium hydroxide gel, calcium phosphate gel or aluminium phosphate gel. Thus, in an alternative embodiment, the methods may be carried out by starting with an aqueous suspension of a composition comprising gIN and an antigen-binding carrier material, such as Algammulin, in order to produce a corresponding composition in which the inulin is in the delta polymorphic form.

The methods may further comprise heating the suspension comprising gamma-inulin at a temperature in a range of from about 60° C. to 70° C. for a time of up to about 1 hour. Typically, the suspension comprising gamma-inulin is heated at a temperature in the range of from about 60-65° C. for inulin particles alone or 65-70° C. for inulin particles containing an antigen carrier, for a time of up to about 1 hour. More typically, the time may be in a range of from about 5 minutes to 30 minutes. Particles of inulin in the delta polymorphic form, or of a composition comprising inulin in the delta polymorphic form and an antigen-binding carrier material, may be isolated from the suspension by centrifugation or other means such as filtration.

The present invention moreover provides the delta inulin prepared in accordance with the methods as described above.

The present invention further provides for methods for the preparation of gamma inulin, wherein said method comprises:
(a) preparing a suspension of particles of inulin in a delta polymorphic form;
(b) optionally fragmenting said particles in said suspension;
(c) recrystallising inulin from said suspension;
(d) converting said recrystallised inulin to a gamma polymorphic form; and
(e) isolating said gamma-inulin in fine or ultrafine particulate form.

The method may further comprise:
(f) converting said gamma-inulin in fine or ultrafine particulate form to delta-inulin in fine or ultrafine particulate form.

As noted above, the dIN is initially observed in the form of "ghosts" which are partially fragmented on heating above 50° C., preferably in the range of from about 60° to 72° C., forming ghost fragments which may serve as multiple micronuclei for subsequent recrystallisation in the fine or ultra-fine form. The optional fragmentation of the suspension in step (b) may therefore comprise either the application of shear stress or ultrasonication while applying a temperature in a range of from about 60° C. to 72° C. In step (c), the inulin may be recrystallised from the suspension at a temperature substantially below 37° C., for example at about 5° C., on the crystallisation micronuclei produced by fragmentation of the dIN, forming ultra-fine particles. The recrystallised inulin in fine or ultra-fine particulate form may be converted to the gamma polymorphic form in step (d) by heating a suspension of the recrystallised inulin at a temperature in the range of from about 25° to 47° C. for up to 1.5 hours, more typically at a temperature of about 45° for a time in a range of from about 15 to 60 minutes. The thus-formed insoluble gIN is then isolated from the suspension, for example, by centrifugation.

The prepared inulin may comprise a majority of particles with a diameter less than 1 μm. The diameter may be in a range of from about 50 nm to 600 nm.

In an alternative embodiment, this method may be carried out with a suspension of a composition comprising dIN and an antigen-binding carrier material, in order to isolate a corresponding composition comprising gIN or dIN and the antigen-binding material in fine or ultra-fine particulate form.

The present invention further provides for the gamma inulin and/or delta inulin prepared in accordance with the method as described above.

The use of gIN or compositions comprising gIN and an antigen-binding carrier material, such as Algammulin, as an adjuvant or other active component in immunotherapeutic preparations is disclosed in U.S. Pat. Nos. 4,954,622, 5,051,408 and 5,476,844, the contents of which are incorporated herein by reference. As described in these US patents, such immunotherapeutic preparations may be formulated in a pharmaceutically or veterinarily-acceptable diluent or carrier in a form suitable for injection, or a form suitable for oral, rectal, vaginal, topical, nasal or ocular administration. The immunotherapeutic preparation may also comprise a second active component which is an immune modulator, for example, an immune modulator such as a vaccinating antigen, an antigenic peptide sequence, or an anti-idiotype immune globulin. Alternatively, the immune modulator may be a lymphokine or cytokine, a thymocyte stimulator, a macrophage stimulator, an endotoxin or even a whole microbe.

Activation of the APC in a human or non-human animal patient by administration of an effective amount of an immunotherapeutic preparation may be used in enhancement of an immune response in a patient, for example for the treatment of an infection by a bacterium, mycoplasma, fungus, virus, protozoan or other microbe, or of an infestation by a worm or parasite. Alternatively, enhancement of the immune response may be used in treatment of an immune disorder such as allergic or rheumatic diseases, immune deficiency diseases, or neurological or gastrointestinal disorders relating to dysfunction of the immune system. In addition, administration of an immunotherapeutic preparation in accordance with the present invention may be used as an anti-tumour treatment. Further details of these immunotherapeutic preparations and methods of treatment are described in U.S. Pat. Nos. 4,954,622, 5,051,408, and 5,476,844,—see also Cooper, P. D. and Carter, M., (1986) *Molec. Immunol.* 23(8):903-908.

Accordingly, the present invention also provides for immunological compositions comprising the gamma inulin and/or delta inulin produced by the methods described above together with a pharmaceutically acceptable carrier, diluent or excipient.

The present invention further provides for immunological compositions comprising the gamma inulin and/or delta inulin produced by the methods described above together with an antigen-binding carrier material. The antigen-binding carrier material may comprise at least one of aluminium hydroxide gel, calcium phosphate gel or aluminium phosphate gel.

In general, suitable compositions for use in accordance with the methods of the present invention may be prepared according to methods and procedures that are known to those of ordinary skill in the art and accordingly may include a pharmaceutically acceptable carrier, diluent and/or adjuvant.

Compositions may be administered by standard routes. In general, the compositions may be administered by the parenteral (e.g., intravenous, intraspinal, subcutaneous or intramuscular), oral or topical route. Administration may be systemic, regional or local. The particular route of administration to be used in any given circumstance will depend on a number of factors, including the nature of the condition to be treated, the severity and extent of the condition, the required dosage of the particular compound to be delivered and the potential side-effects of the compound.

In general, suitable compositions may be prepared according to methods which are known to those of ordinary skill in the art and may include a pharmaceutically acceptable diluent, adjuvant and/or excipient. The diluents, adjuvants and excipients must be "acceptable" in terms of being compatible with the other ingredients of the composition, and not deleterious to the recipient thereof.

Examples of pharmaceutically acceptable carriers or diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

The compositions of the invention may be in a form suitable for administration by injection, in the form of a formulation suitable for oral ingestion (such as capsules, tablets, caplets, elixirs, for example), in the form of an ointment, cream or lotion suitable for topical administration, in a form suitable for delivery as an eye drop, in an aerosol form suitable for administration by inhalation, such as by intranasal inhalation or oral inhalation, in a form suitable for parenteral administration, that is, subcutaneous, intramuscular or intravenous injection.

For administration as an injectable solution or suspension, non-toxic parenterally acceptable diluents or carriers can include, Ringer's solution, isotonic saline, phosphate buffered saline, ethanol and 1,2 propylene glycol.

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl distearate which delay disintegration.

Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The emulsions for oral administration may further comprise one or more emulsifying agents. Suitable emulsifying agents include dispersing agents as exemplified above or natural gums such as guar gum, gum acacia or gum tragacanth.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein.

The topical formulations of the present invention, comprise an active ingredient together with one or more acceptable carriers, and optionally any other therapeutic ingredients. Formulations suitable for topical administration include liquid or semi-liquid preparations suitable for penetration through the skin to the site of where treatment is required, such as liniments, lotions, creams, ointments or pastes, and drops suitable for administration to the eye, ear or nose.

Drops according to the present invention may comprise sterile aqueous or oily solutions or suspensions. These may be prepared by dissolving the active ingredient in an aqueous solution of a bactericidal and/or fungicidal agent and/or any other suitable preservative, and optionally including a surface active agent. The resulting solution may then be clarified by filtration, transferred to a suitable container and sterilised. Sterilisation may be achieved by: autoclaving or maintaining at 90° C.-100° C. for half an hour, or by filtration, followed by transfer to a container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those described above in relation to the preparation of drops. Lotions or liniments for application to the skin may also include an agent to hasten drying and to cool the skin, such as an alcohol or acetone, and/or a moisturiser such as glycerol, or oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols.

The composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

The compositions may also be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which is incorporated herein by reference.

For the purposes of the present invention molecules and agents may be administered to subjects as compositions either therapeutically or preventatively. In a therapeutic application, compositions are administered to a patient already suffering from a disease, in an amount sufficient to cure or at least partially arrest the disease and its complications. The composition should provide a quantity of the molecule or agent sufficient to effectively treat the patient.

The therapeutically effective dose level for any particular patient will depend upon a variety of factors including: the disorder being treated and the severity of the disorder; activity of the molecule or agent employed; the composition employed; the age, body weight, general health, sex and diet of the patient; the time of administration; the route of administration; the rate of sequestration of the molecule or agent; the duration of the treatment; drugs used in combination or coincidental with the treatment, together with other related factors well known in medicine.

One skilled in the art would be able, by routine experimentation, to determine an effective, non-toxic amount of agent or compound which would be required to treat applicable diseases and conditions.

Generally, an effective dosage is expected to be in the range of about 0.0001 mg to about 1000 mg per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; about 5.0 mg to about 15 mg per kg body weight per 24 hours.

Alternatively, an effective dosage may be up to about 500 mg/m². Generally, an effective dosage is expected to be in the range of about 25 to about 500 mg/m², preferably about 25 to about 350 mg/m², more preferably about 25 to about 300 mg/m², still more preferably about 25 to about 250 mg/m², even more preferably about 50 to about 250 mg/m², and still even more preferably about 75 to about 150 mg/m².

Typically, in therapeutic applications, the treatment would be for the duration of the disease state.

Further, it will be apparent to one of ordinary skill in the art that the optimal quantity and spacing of individual dosages will be determined by the nature and extent of the disease state being treated, the form, route and site of administration, and the nature of the particular individual being treated. Also, such optimum conditions can be determined by conventional techniques.

It will also be apparent to one of ordinary skill in the art that the optimal course of treatment, such as, the number of doses of the composition given per day for a defined number of days, can be ascertained by those skilled in the art using conventional course of treatment determination tests.

The present invention also provides for immunotherapeutic preparations for activation of the alternative pathway of complement (APC) in a human or non-human animal patient, wherein said preparations comprise particles of gIN or dIN in fine or ultra-fine particulate form, or particles comprising gIN or dIN and an antigen-binding carrier material in fine or ultra-fine particulate form, prepared by the methods as broadly described above.

The present invention further provides for methods for the activation of the APC in a human or non-human animal patient, wherein said method comprises administration to said patient an effective amount of at least one of the immunotherapeutic preparations as broadly described above.

Accordingly, the present invention provides for methods for stimulating an immune response, wherein said methods comprise administering to a subject a therapeutically effective amount of an immunotherapeutic agent comprising:
(a) the inulin as described above; or
(b) the immunological composition as described above.

The immune response may comprise activation of the alternative pathway of complement.

The present invention further provides for methods for enhancing an immune response, wherein said methods comprise administering to a subject a therapeutically effective amount of an adjuvant, wherein said adjuvant comprises:
(a) the inulin as described above; or
(b) the immunological composition as described above.

The present invention moreover provides methods for treating cancer, wherein said methods comprise administering to a subject a therapeutically effective amount of:
(a) the inulin as described above; or
(b) the immunological composition as described above.

The present invention additionally provides for the use of the immunotherapeutic preparations as described above in the manufacture of a medicament for administration to a human or non-human animal patient to activate the APC in a patient.

The present invention will now be described with reference to specific examples, which should not be construed as in any way limiting the scope of the invention.

EXAMPLES

Example 1

Materials and Methods

The materials and procedures for preparation of standard formulations of gIN and Algammulin have been described elsewhere—see Cooper and Carter, (1986) and Cooper and Steele, (1991) supra.

1.1 Estimation of the Distribution of Particle Size within Inulin Preparations and Derived Compositions It was necessary to monitor particle size of inulin and its derived compositions during preparation and in the final product. Several methods were used for this purpose in the present invention, most of which are suitable only for relative comparisons. The results were generally consistent, as shown in Table 1. It was desirable that a majority of the particles be under 1 µm in diameter.

1.1(a) Particle Counters

Particle size was advantageously estimated by Fluorescence Activated Cell Sorting flow cytometry ('FACS analysis') using forward scatter (FSC) and side scatter (SSC) characteristics. A Becton Dickinson FACScalibur was used at voltages of FSC: E-01/9.99 and SSC: 211/1.98 and number of channels plotted on a logarithmic scale. The particle size was directly correlated with the number of channels used in FSC. Preliminary calibrations using a 6 µm latex standard particle preparation indicated that 1 µm was equivalent to approximately FSC channels 4 to 6. As presently available, FACS analysis could not detect particles in FSC channels less than 2 or 3 (ca 0.5 µm). For this reason, the 'FSC median sizes' quoted referred only to those particles detectable above this threshold, and so the true median sizes of those finer preparations whose scans overlap the threshold were usually less than the measured median.

1.1(b) Haemocytometer

Particles greater than 1 µm diameter were visualised in the haemocytometer and a visual estimate made of the diameter of the majority class of particle. Experience determined that this was usually an underestimate, but was useful for comparative purposes. Electron microscopy (EM) was previously used to measure particle sizes (Cooper and Steele, 1991), but more recent correlations have shown that EM measurements were also an underestimate compared with measurements made on hydrated particles, probably because of shrinkage on drying for EM examination. Thus the preparations yielding the EM particles measuring 2-3 µm and illustrated in U.S. Pat. Nos. 4,954,622 and 5,051,408 and in Cooper and Steele (1991) have subsequently been shown to have peak size distributions between 6 and 12 µm, with very little content below 1 µm, when examined in hydrated form by FACS analysis (see FIG. 8).

1.1(c) Density/Viscosity Sedimentation

Provided the densities are similar, for example among gIN preparations on the one hand, or among Algammulin preparations with a similar alum content on the other, a quick relative estimate was able to be made by layering 50 µl of the preparation on 500 µl Percoll colloid (density=1.125 g/ml) for Algammulin, or 50% (v/v in distilled water) Percoll colloid for gIN, and centrifuging in 5 mm diameter plastic tubes at 3500 rpm (2400 g) for 15 min in 5 min periods. One or more preparations of known characteristics were treated in parallel as standards. The tubes were viewed after each period and the pellet and overlay sizes and turbidities were compared visually with the standards. Smaller particles sedimented more slowly (Table 1). Preparations containing particles less than 1 µm deposited only a trace pellet.

1.1(d) Optical Density

As disclosed previously for Algammulin (Cooper and Steele, 1991), the $OD_{700}$ of a 1/100 dilution (0.5 mg/ml) of gIN in PBS was lower for smaller particle sizes (Table 1). An $OD_{700}$ (0.5 mg/ml) of <0.15 was seen as desirable.

1.1(e) Pellet Density

As disclosed previously for Algammulin (Cooper and Steele, 1991), the pellet densities of gIN preparations after strong centrifugation (eg 7 min at 13000 rpm in an Eppendorf angle centrifuge, yielding a clear supernatant) were lower for smaller particles (Table 1). A pellet density of <100 mg/ml was seen as desirable.

1.2 Proportion of Inulin Suspensions Present in the Gamma Form

Portions of 50 µl of inulin suspensions (ca 50 mg/ml) were diluted in glass tubes containing 5 ml PBS and the $OD_{700}$ was measured (OD1). The tubes were then immersed in a water bath at 37° C. for 10 min, cooled and the $OD_{700}$ was measured again (OD2). The percentage of inulin present in the gamma form was then taken as OD2×100/OD1. A gIN content of >90% was seen as desirable.

1.3 Proportion of Inulin Suspensions Present in the Delta Form

Portions of 200 µl of inulin suspensions (ca 50 mg/ml) were diluted in glass tubes containing 4.8 ml PBS and the $OD_{700}$ was measured (OD1). The tubes were then immersed in a water bath at 50° C. for 10 min, cooled and the $OD_{700}$ was measured again (OD2). The percentage of inulin present in the delta form was then taken as OD2×100/OD1%. A maximum dIN content >40%, more preferably >85%, was seen as desirable.

TABLE 1

Properties of gamma inulin preparations relating to particle size. ND = Not determined.

| gIN pre-paration | $OD_{700}$ 0.5 mg/ml | Percoll estimate of relative size | FSC relative size | Haemocytometer estimate of mean diameter (microns) | Pellet density mg/ml |
|---|---|---|---|---|---|
| gIN-0795 | 0.1 | 0.2 | ND | ND | 88 |
| gIN-0195 | 0.135 | 0.1 | <7 | <1 | 91 |
| gIN-0495 | 0.264 | 0.5 | 6 | <1 | 119 |
| gIN-1285 | 0.292 | 1 | 22 | 2-3 | 156 |
| gIN-0487 | 0.37 | 2 | 30 | ND | 225 |
| gIN-1196 | 0.741 | 5 | ND | 10 | 250 |

Example 2

Formation of Delta Inulin

Although the turbidity of a dilute suspension (0.5 mg/ml) of gIN particles has previously been demonstrated to clear almost completely over a narrow temperature range (47-49° C.; Cooper and Steele, 1991), a small residue (<0.5% of the original $OD_{700}$) does not dissolve until the temperature exceeds 80° C. In addition, it has been observed that if inulin powder as received (ie unprocessed) is dissolved in water by slow warming (for example in a water bath) to 80° C., a fine cloudiness usually remains that impedes sterile filtration. In contrast, if the same powder is dissolved by rapid heating (eg over a gas flame) to 80° C., a clear solution results that filters easily.

The implication is that a component is formed during processing that only dissolves at temperatures higher than the temperature at which gIN dissolves. This component is termed delta inulin, and is monitored by $OD_{700}$ measurements on dilute suspensions as described in Methods. FIG. 1 shows that a temperature of 65-68° C. was sufficient to dissolve the majority of this residue, so that its optimum temperature of formation was lower than 65° C.

Figure 2:
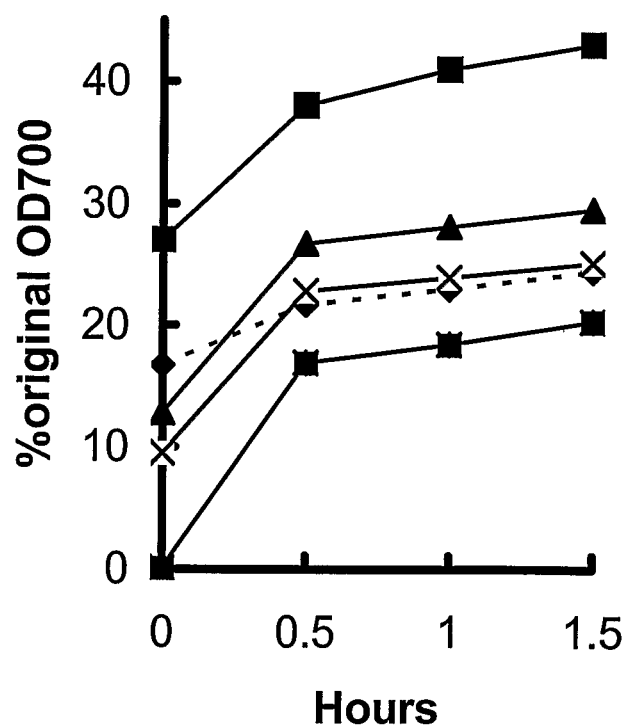
FIG. 2 shows the increase in dIN content of five standard formulations of gIN (50 mg/ml) with time of incubation at 56° C. (from top to bottom: gIN-1196A, gIN-1196, gIN-0397B, gIN-0996, gIN-0497). Samples of 0.2 ml taken at intervals into 4.8 ml PBS were then heated for 10 min at 50° C. for $OD_{700}$ assay of dIN content.

To investigate this further, 1.5 ml aliquots of a 50 mg/ml suspension of various preparations of gIN and Algammulin were immersed in a 56° C. water bath and 0.2 ml samples were diluted at intervals into 4.8 ml cold PBS, for the standard dIN assay (Methods). FIG. 2 shows that the dIN content of gIN preparations increased progressively to a maximum value, and that this 'dIN capacity' varied with different preparations. The same properties were shown by Algammulin preparations. Many gIN and Algammulin preparations contained very little dIN before such heating. Further tests showed that this capacity was reached by heating for 3 hr at 56° C., and that yields were higher by heating at 55° C.

Example 3

Properties of Delta Inulin

A larger preparation of material enriched in dIN was made as follows. A standard formulation of gIN (200 ml at 50 mg/ml) was incubated for 1 hr in a water bath at 56° C., which was then raised to 60° C. for 30 min. The particles were centrifuged, resuspended in water at 60° C., re-incubated at 60° C. and washed again in the same manner, being finally resuspended in 50 ml cold water. This treatment was sufficient to remove much of the inulin present in the alpha and gamma forms. The end material was a grey, gelatinous paste, contrasting with the fluid milky whiteness of the alpha and gamma forms. In the haemocytometer, large (>5 mµ), faint ghost-like particles were seen, in contrast to the smaller (<5 mµ) sharply demarcated particles of gIN.

A sample of this dIN-enriched suspension dissolved completely at 80-85° C. The refractive index was equivalent to 48 mg/ml, yield ca 15% of the starting material. This yield was consistent with the proportion of dIN 'capacity' found by the $OD_{700}$ assay. The addition of 4 volumes of ethanol gave a bulky precipitate. When 1 ml of this ethanolic suspension was at once added to 5 ml water at 23° C., the turbid dilution cleared immediately, but when the suspension was first stood overnight at 23° C. such a dilution remained substantially turbid at 23° C. but cleared at once at 37° C. This is typical of the beta forms of inulin as described earlier (Cooper and Carter, 1986) and mirrors the behaviour of the unprocessed inulin powder as received, when first dissolved.

Further 2 ml samples of the dIN solution were then crystallised with mixing for 4 days at 5° C. or 37° C. to yield fluid, milky white suspensions. The $OD_{700}$ thermal transition curves of 0.5 mg/ml dilutions of these suspensions were typical of the alpha and gamma forms respectively (FIG. 3), with 50% $OD_{700}$ thermal transition points of 36.5° C. and 46.5° C. Incubation of the 37° C. particles for 1 hr at 56° C. completed the cycle, resulting again in material characteristic of the delta form, with a 50% $OD_{700}$ thermal transition point of 56.5° C.

Thus, like the alpha, beta and gamma forms, the delta form is a physical polymorph rather than a chemical modification, and again like the alpha, beta and gamma forms the inulin molecules in the delta polymorph can be re-arranged by dissolution and recrystallisation to all the other previously described polymorphic forms of inulin by appropriate physical manipulation.

Example 4

Figure 4A:
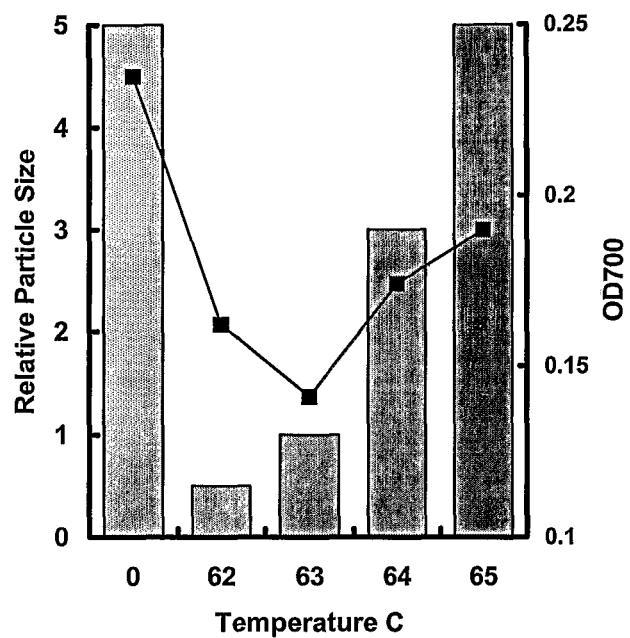
FIG. 4 shows A: Optical densities (points, 0.5 mg/ml) and relative particle sizes (columns), as determined by Percoll colloid centrifugation of 1 ml samples of a pre-heated (56° C.) standard formulation of gIN (gIN-1285) partially fragmented at the indicated temperatures then crystallised at 5° C. and converted to the gamma form; B: comparison of particle size distributions by FACS analysis of a standard formulation of gIN (gIN-0402) treated in the same way (but fragmented at 62.5° C., left hand peak, FSC median size 6.12) and with the same preparation untreated (right hand peak, FSC median size 18.43). The left hand peak thus illustrates a gIN preparation termed "fine" formulation.
Figure 4B:
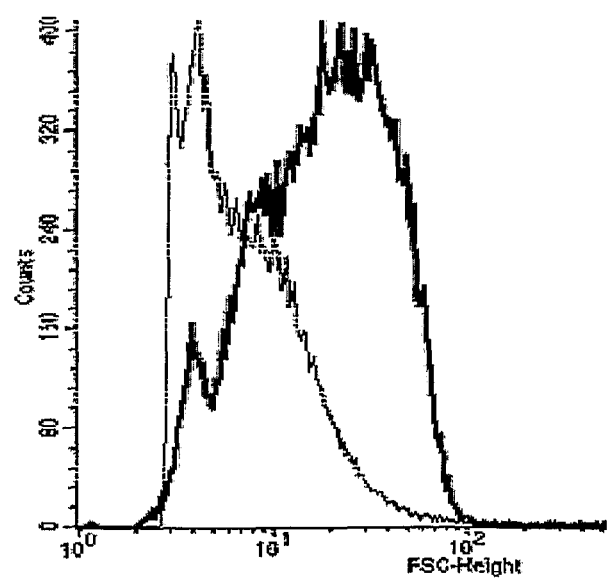
Figure 5A:
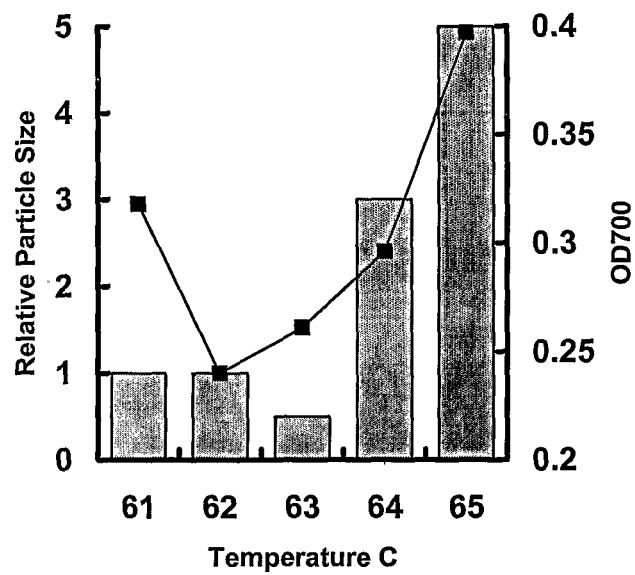
FIG. 5 shows A: Optical densities (points, 0.5 mg/ml) and relative particle sizes (columns), as determined by Percoll colloid centrifugation of 1 ml samples of a pre-heated (56° C.) standard formulation of Algammulin (AG-37) partially fragmented at the indicated temperatures then crystallised at 5° C. and converted to the gamma form; B: comparison of particle size distributions by FACS analysis of a standard formulation of Algammulin treated in the same way (but fragmented at 62.5° C., left hand peak, AG-51, FSC median size 9.22) and with a similar preparation untreated (right hand peak, AG-37, FSC median size 42.55). The left hand peak thus illustrates an Algammulin preparation termed "fine" formulation.
Figure 5B:
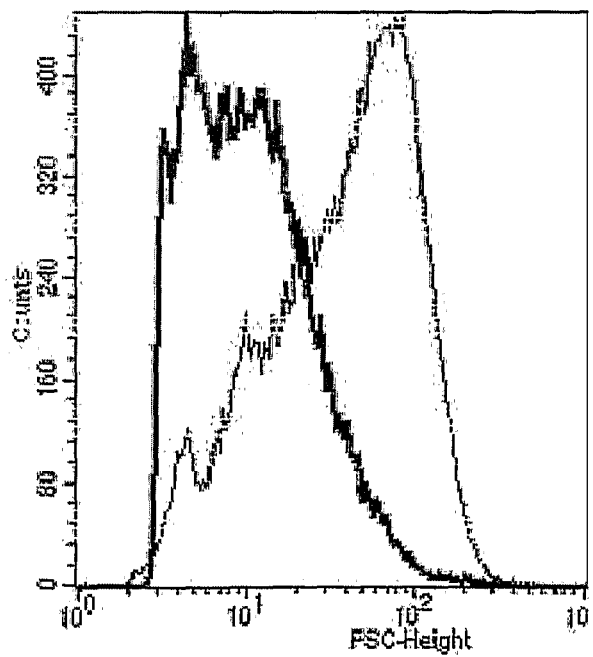

Use of the Delta Polymorph to Recrystallise Inulin and its Derivative Compositions in Smaller Particles After consideration of the data of FIG. 1, preparations of ghosts from standard formulations of gIN and Algammulin were partially fragmented at temperatures between 60° C. and 70° C. In one example, to determine the temperature at which the smallest particles were subsequently obtained by recrystallising from such fragments, 1 ml samples in glass tubes of one of various preparations of gIN pre-heated at 56° C. were, without cooling, stood in water baths for 5 min at either 0° C., 60° C., 61° C., 62° C., 63° C., 64° C. or 65° C. The tubes were chilled in ice then stood at 5° C. for 7 days to crystallise in the alpha form, then converted to the gamma form at 45° C. for 30 min. The $OD_{700}$ was measured at 1/100 dilution in PBS, and their relative particle size estimated by Percoll centrifugation as described in the Methods. FIG. 4A shows that the optimum temperature for a typical pre-heated standard formulation of gIN was 62-63° C., as shown by both Percoll and OD examination, while FIG. 4B compares the particle size distribution of such a standard formulation with that obtained after pre-heating at 56° C. then partial fragmentation at 62.5° C. followed by recrystallisation at 5° C. on these micro-nuclei and conversion to the gamma form. FIG. 5A shows that the optimum temperature for a typical pre-heated standard formulation of Algammulin was also 62-63° C., while FIG. 5B compares the particle size distribution of such a standard formulation with that obtained after pre-heating then partial fragmentation at 62.5° C. followed by recrystallisation at 5° C. and conversion to the gamma form. In both cases partial fragmentation produces a marked reduction in particle size. Preparations made by partial fragmentation of dIN ghosts in this way are referred to as fine formulations.

The partially fragmented ghosts may advantageously be further broken up by shear stress or ultrasonication while maintaining an elevated temperature. Such preparations are referred to as ultra-fine preparations.

Figure 6A:
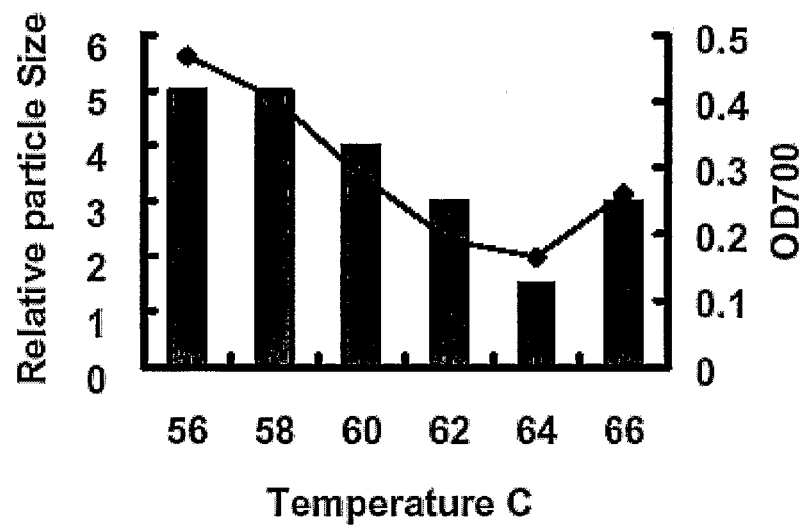
FIG. 6 shows A: Optical densities (points, 0.5 mg/ml) and relative particle sizes (columns), as determined by Percoll colloid centrifugation of 1 ml samples of a standard formulation of gIN (gIN-0803) pre-heated at 55° C., partially fragmented at the indicated temperatures and subjected to shear stress while hot (ie passed through a 30 gauge hypodermic needle), then crystallised at 5° C. and converted to the gamma form; B: comparison of particle size distributions by FACS analysis of a fraction fragmented in this way at 65° C. (left hand peak, FSC median size 3.32) and with the same preparation untreated (right hand peak, FSC median size 8.20). The left hand peak thus illustrates a gIN preparation termed "ultra-fine" formulation and made using shear stress fragmentation.
Figure 6B:
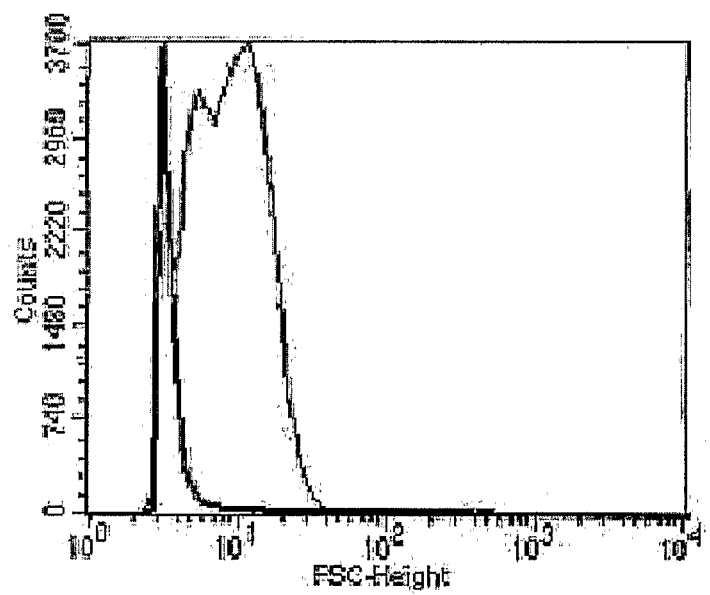

Shear stress may involve use of a Microfluidisation™ apparatus, or may be achieved by passing the hot, partially fragmented ghost suspension through fine orifices such as 27 or 30 gauge hypodermic needles attached to a syringe. FIG. 6 compares the particle size distribution of a typical standard formulation of gIN with that obtained by shear stress, that is by pre-heating such a formulation at 55° C., partial fragmentation at 65° C., passing through a 30 gauge needle while hot followed by recrystallisation at 5° C. on these micro-nuclei and conversion to the gamma form.

Figure 7:
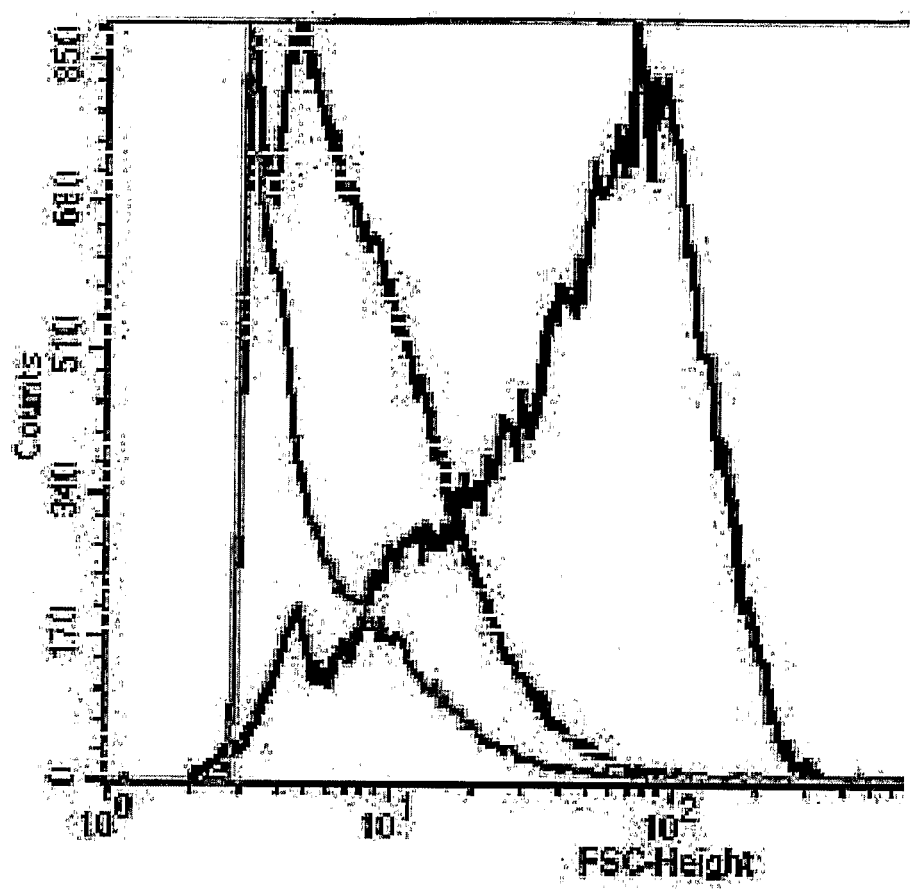
FIG. 7 shows a comparison of particle size distributions by FACS analysis of a standard formulation of Algammulin (right hand peak, AG-41, FSC median size 48.70) and with the same preparation pre-heated at 56° C., partially fragmented at 65° C. and either subjected to one cycle of ultrasonication while hot, then crystallised at 5° C. and converted to the gamma form (central peak, AG-42, FSC median size 6.49) or to two complete cycles of the same treatment (left hand peak, AG-43, FSC median size 4.49). The central and left hand peaks thus illustrate two Algammulin preparations termed "ultra-fine" formulations and made using ultrasonic disruption.

Ultrasonication was accomplished by immersing a clean, sterilised ultrasonic probe in a partially fragmented ghost preparation kept between 60° C. and 70° C. (by cooling if necessary) and run at a suitable wattage for a time sufficient to reduce the $OD_{700}$ of a 1/4 dilution in PBS of the ghost preparation to a predetermined level, typically in a range of from 1 to 10%. This level was calibrated by a method similar to that described above to determine the optimum temperature for ghost fragmentation at which subsequent recrystallisation gave the smallest particles. FIG. 7 shows the particle size distribution of a typical standard formulation of Algammulin, and compares it with the smaller particle size obtained by pre-heating that preparation at 56° C., followed by one cycle of ultrasonication at 65° C. then re-crystallization on these micro-nuclei at 5° C. and conversion to the gamma form. FIG. 7 also shows the further reduction in particle size obtained when the same preparation is subjected to two complete cycles of this treatment, that is pre-heating, partial fragmenting at 62-70° C., ultrasonication of partially fragmented ghosts then recrystallisation at 5° C. and conversion to the gamma form.

Example 5

Figure 8:
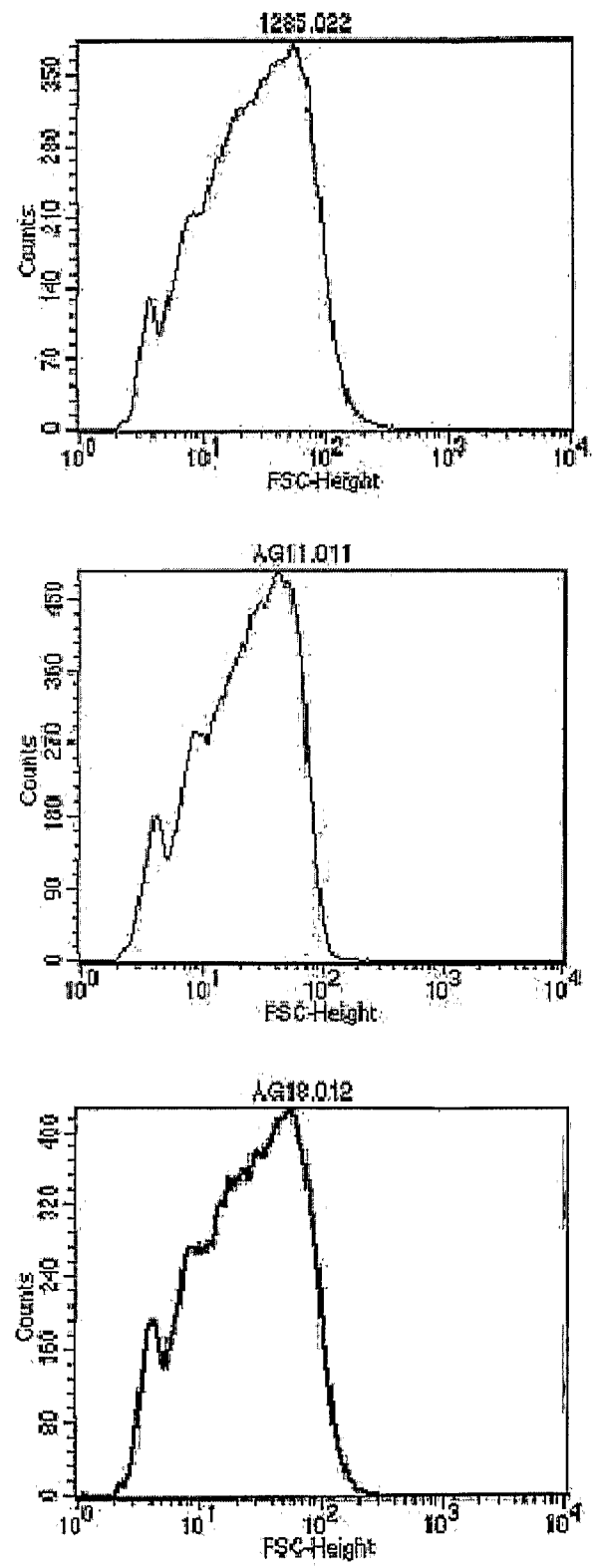
FIG. 8 shows a comparison of particle size distributions by FACS analysis of the standard formulations of gIN (gIN-1285, FSC median size 26.42) and Algammulin (AG-11, FSC median size 23.93 and AG-18, FSC median size 24.80) described in U.S. Pat. Nos. 4,954,622 and 5,051,408.
Figure 9:
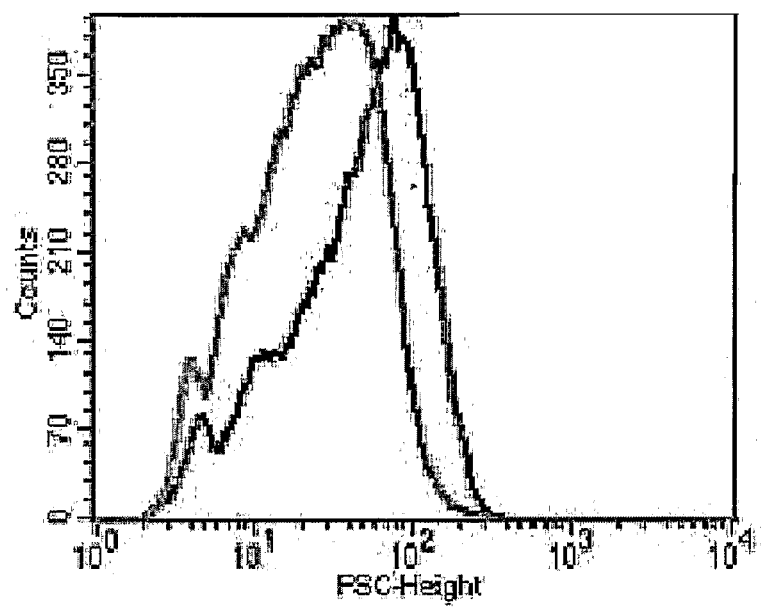
FIG. 9 shows a comparison of particle size distributions by FACS analysis of a standard formulation of Algammulin (right hand peak, AG-41, FSC median size 48.70) and the same preparation vigorously treated with an ultrasonic disruption device (left hand peak, AG-41u, FSC median size 24.14).

Failure of Earlier Preparations to Achieve a Significant Proportion of Particles <1 µm in Diameter The earlier US patents referred to herein (and Cooper and Steele, 1988, Cooper and Steele 1991, and Cooper, McComb and Steele 1991) describe gIN lot gIN-1285 and Algammulin lots AG-11 and AG-18. These were all standard formulations and showed majority particle diameters (by EM measurement) of 2-3 µm. Haemocytometer estimates seemed similar or somewhat less. However, more recent measurements using FACS analysis show clearly that the majority of particles in hydrated form were much larger, being 6-12 µm in diameter (FIG. 8). The proportion of particles in the desirable range of <1 μm was negligible.

Vigorous treatment with an ultrasonic disruption device of both gIN and Algammulin particles produced visible changes in the preparations. Care was needed to keep the temperatures below 70° C. The suspensions became much more viscous, the pellet densities and $OD_{700}$ (diluted 1/100) decreased and the particles sedimented much more slowly in viscosity/density gradient tests. Such changes in these relative or indirect parameters were taken to demonstrate marked decreases in particle diameter, as indicated in U.S. Pat. No. 5,476,844. However, when examined by FACS analysis it was clear that the decreases in size were modest (FIG. 9 for Algammulin, lot AG-41u compared with the original material AG-41; gIN showed even less change, data not shown) and that no significant proportion was <1 μm in diameter after ultrasonic treatment. It was concluded that this treatment substantially damaged the structure of the particles, possibly by local heating effects, but did not greatly decrease their diameter. It was also concluded that the relative or indirect parameters described were only applicable to freshly crystallised, undamaged particles.

Example 6

Advantages of the Ultrafine Formulation

This example demonstrates that inulin preparations of smaller particle sizes were more potent in activating the APC, had higher adjuvant activity, and produced less local reaction upon subcutaneous injection.

6.1 Samples for Testing

Five batches of gIN were selected as having as wide a range of mean particle diameters as possible, from ca 10 μm (standard preparation) to ca 500 nm (ultra-fine preparation). The finer preparations had been re-crystallized from standard preparations on dIN micronuclei as described in Example 4, after a variety of shear stress or sonication treatments at temperatures between 60 and 70° C. Samples of each batch were (1) heated at 45° C. for 10 min to minimise co-crystallised alpha and beta inulin, diluted 10-fold in water while hot, centrifuged and resuspended to 50 mg/ml as enriched gIN, or (2) heated at 55° C. for 3 hr to convert to the delta form and minimise co-crystallised gamma, alpha and beta inulin, then washed and resuspended as for the gamma samples to give enriched dIN. Table 2 summarizes some properties, and FIG. 10 shows the differences in OD thermal transition curves for the ultra-fine samples. The six standard preparations were similar. These transition curves were measured by progressively heating 5 ml PBS containing 0.5 mg/ml inulin in glass tubes as described in FIG. 3. In such tests gIN was shown to have a 50% thermal transition point of 48±1° C. (Cooper & Steele 1991a) and dIN of 57±3° C. The two polymorphic forms were clearly distinguished by this test.

TABLE 2

Properties of Inulin Preparations of Different Particle Sizes
and Polymorphic Forms for Assays of Complement Activation,
Adjuvanticity and Local Toxicity

| | Gamma form | | | | Delta form | | | |
|---|---|---|---|---|---|---|---|---|
| Source | % gamma | % delta | FSC mean | mg/ml | % gamma | % delta | FSC mean | mg/ml |
| gIN0402 (standard) | 95.6 | 0 | 164 | 50 | 12 | 88 | 119 | 50 |
| gIN0602 (standard) | 68.1 | 31.9 | 212 | 50 | 9.6 | 90.4 | 123 | 50 |
| gIN1285 (standard) | 72.5 | 27.5 | 70.8 | 50 | 10 | 90 | 37 | 50 |
| CT2D (ultra-fine) | 82.6 | 17.4 | 28.9 | 50 | 5.1 | 94.9 | 21.4 | 37 |
| CT2F (ultra-fine) | 85 | 15 | 12.9 | 45 | 5.8 | 94.2 | 12.1 | 43 |

6.2 Assay of Alternative Pathway of Complement Activation by Inulin Preparations 6.2(a) Assay Procedure The assay used measured the colour produced by the spontaneous lysis of unsensitised rabbit RBC by the alternative pathway of complement (APC) of normal human serum, in a form of back titration that assayed the amount of APC activity remaining after first incubating a set volume of human serum with different concentrations of inulin for a specified time. Activated complement is very labile, so that activation results in its immediate depletion.

The method used was a variant of that of Hoffmann, L. G. & Mayer M. M. (1977), in: Williams C. A. and Chase M. W. (eds.), *Methods in Immunology and Immunochemistry* Vol. 4, pp. 137-166, Academic Press, New York. The buffer (Veronal) included EGTA to block classical pathway complement activity, and magnesium to permit the alternative pathway to function in the presence of the chelating agent. The primary incubation was for 20 min at 37° C. (190 µl serum+10 µl buffer containing 0 (control), or 1.0 to 10 µg inulin), stopped by adding 1 ml cold buffer (15 min at 0° C. to chelate calcium), after which the serum samples were diluted with buffer at 0° C. (120-400 µl serum to a total volume of 500 µl). At 10-second intervals 500 µl of prepared RBC was added and the tubes were placed in a shaking water bath at 37° C. for the secondary incubation. After 30 min lysis was stopped by addition of 4 ml cold 0.15 M NaCl. The tubes were centrifuged and the supernatant absorbance at 414 nm was measured in a spectrophotometer. This value was expressed as a percentage of the absorbance of the same concentration of RBC in water (100% lysis). Each reading was a mean of triplicate assay tubes. The serum was a pool taken from four volunteers and stored in 0.4 ml aliquots at −20° C. New pools, as required, were calibrated against the previous pool with a standard inulin preparation.

6.2(b) Interpretation of the Assay

Figure 11:
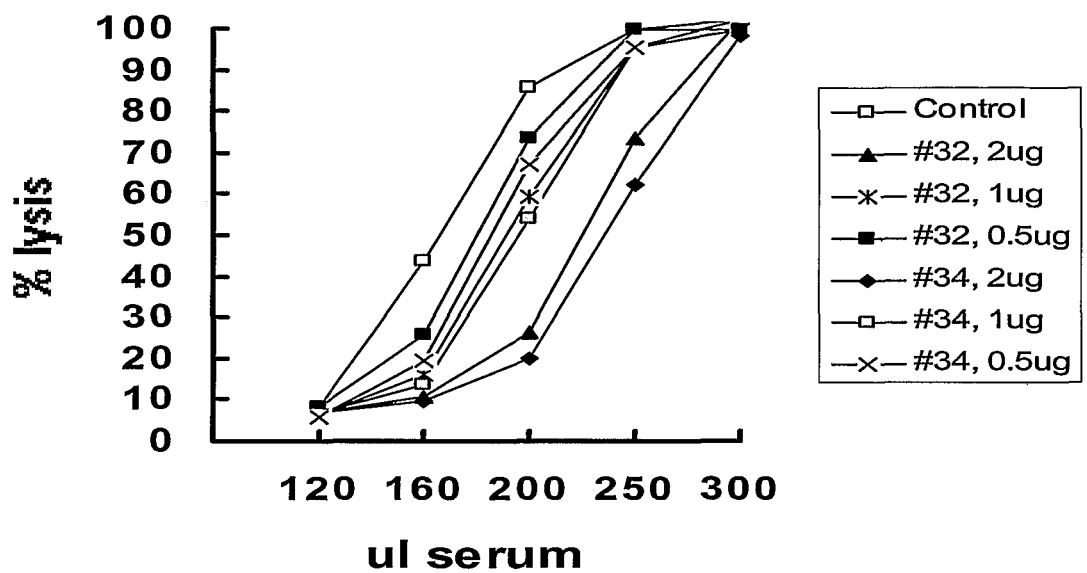
FIG. 11 shows the results obtained when different volumes of human sera were pre-incubated with either saline (control) or different amounts of two ultra-fine gIN preparations (gIN-32 and gIN-34) and then allowed to lyse rabbit RBC. After centrifugation the optical density was expressed as a percentage of that of replicate RBC samples incubated with water alone (100% lysis).

A plot of the volume of serum added against the percentage of cells lysed showed a smooth sigmoid curve (Control in FIG. 11). Tubes pre-incubated with inulin also gave smooth sigmoid curves (other curves of FIG. 11), but displaced to the right.

Figure 12:
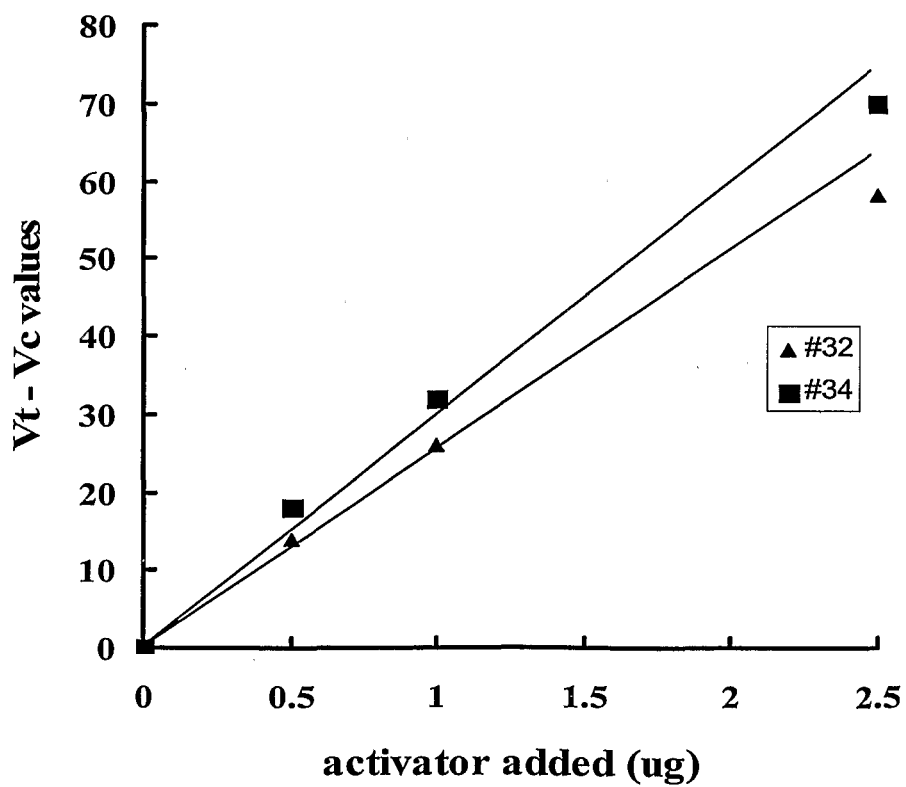
FIG. 12 shows the relation between the weight of inulin added to the pre-incubations described in FIG. 11 and the degree of lysis resulting from the secondary incubation, expressed as the difference between the volume of serum giving 50% lysis in the test curves and that of the control (Vt-Vc values).

It was assumed that the amount of complement activity present in the tube that allowed a given degree of lysis, say 50%, was always the same under the same defined conditions, and could be represented by some constant (K) times the volume of serum giving that amount of lysis. Taking the amount of complement activity present at 50% lysis as $KV_c$ (where $V_c$ is the volume of serum giving 50% lysis in the control), then the amount of complement depleted by the activator in the pre-incubation would be $[KV_t-KV_c]$, where $V_t$ is the volume of serum giving 50% lysis after being depleted by the activator. Activities could be expressed in this way as µl serum. In FIG. 12, a plot for two inulin preparations of $[V_t-V_c]$ values against µg inulin added gave virtually linear dose-responses (since zero activator dose gave a zero $[V_t-V_c]$ value, the lines went through the origin). This was a good confirmation of the legitimacy of the assumptions and of the accuracy of the test. The relative activities of different activators at 1 µg per tube could therefore be compared by their $[V_t-V_c]$ values, as the constant K cancels out.

The $[V_t-V_c]$ values were measured for various inulin preparations at several concentrations as per FIG. 12 and the mean value for 1 µg was expressed as $100 \times [V_t-V_c]/V_c$, the AP activity conveniently being referred to as the percentage of the serum spent, or exhausted, by 1 µg of the activator under the standard conditions of the test. To minimise variation, inulin concentrations were planned so that the $[V_t-V_c]$ value observed was 20% to 60% of $V_c$.

6.2(c) Results

Figure 13:
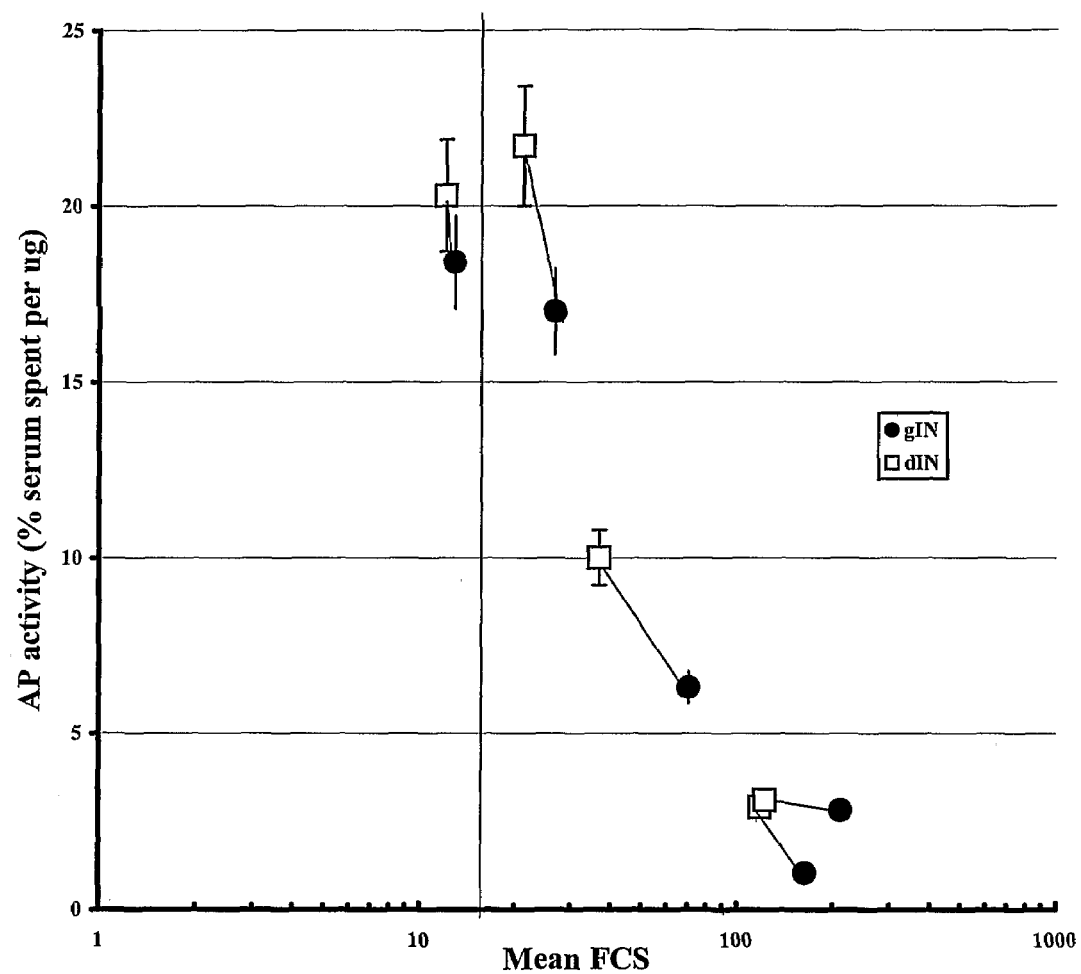
FIG. 13 compares the mean particle diameter obtained by FACS forward scatter analysis ('FSC means' as described in Example 1a) of the ten samples described in Table 2 with their ability to activate the alternative complement pathway ('AP activity', expressed as their [Vt-Vc] values per μg obtained as illustrated in FIG. 12). The connector lines join gamma-delta pairs from the same source preparation.
Figure 14:
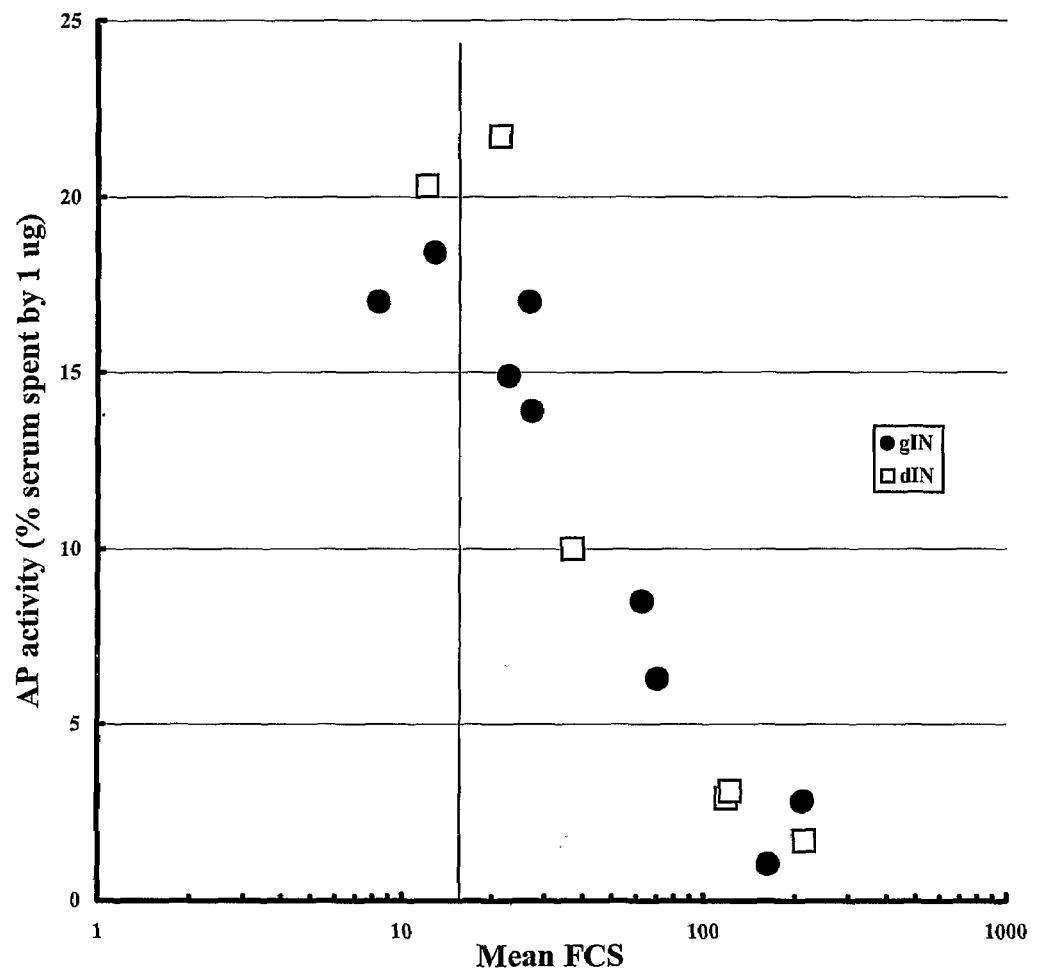
FIG. 14 replicates the presentation of FIG. 13 with the inclusion of all other assessable samples available. The vertical line represents 1 μm as estimated from scans including a 6 μm latex standard.

The mean particle size (by FACS analysis, see Example 1a) and APC activity of the ten samples described in Example 6.1 above were compared in FIG. 13. It was seen that APC activity increased markedly with a decrease in particle size for both gamma and delta polymorphs, but that dIN was consistently more active than the gamma form. The connector lines indicate the pairs from each original preparation. The error bars show the standard errors of the mean, based on 8 to 11 duplicate assays in each case. A similar graph of all assessable preparations available (FIG. 14) reinforced this trend. The vertical line represents 1 µm, as estimated from a 6 µm latex particle standard, and the data points lying to the left of this line represent preparations of diameters in the range of 500-1000 nm.

6.3 Adjuvant Activity of Inulin Preparations

Figure 15:
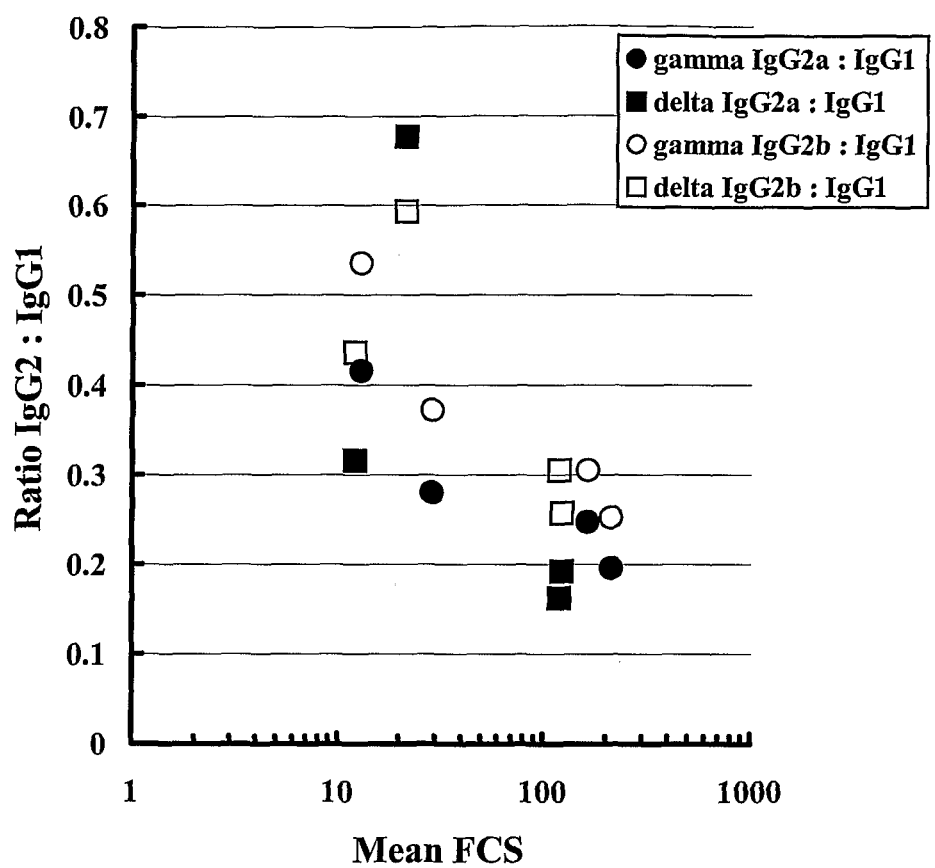
FIG. 15 shows the ratio of specific antibody subtypes IgG2a and IgG2b to IgG1 (ELISA) in the sera from mice (BALB/c, 8 per group) injected intramuscularly with 1 μg vaccine grade hepatitis B surface antigen plus 500 μg of gamma or delta inulin (preparations 1 to 8, Table 2). Mice were boosted at 14 days and bled at 28.

Groups of mice were injected with hepatitis surface antigen plus one of eight of the gamma or delta inulins listed in Table 2. The proportional increase in specific IgG1, IgG2a and IgG2b in their sera compared with parallel titres from injection with antigen alone were expressed as the ratios of IgG2a or IgG2b to IgG1. FIG. 15 presents these in terms of particle size (mean FCS readings) as per FIGS. 13 and 14, and shows that both gamma and delta ultra-fine preparations tend to shift the emphasis towards the IgG2 species compared with standard preparations. This is a desirable outcome as it suggests that Th1 responses are enhanced with a decrease in particle size. This reinforces the same tendency of gamma inulin (Cooper & Steele, 1988).

Figure 16:
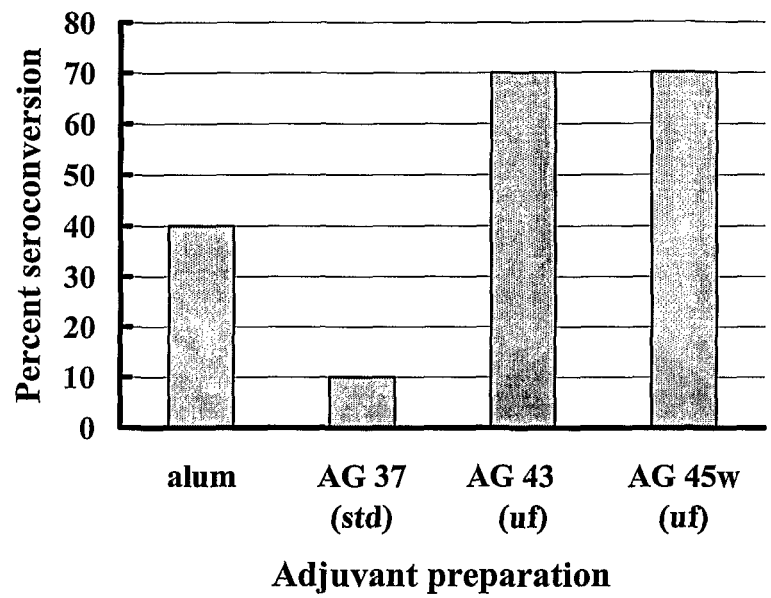
FIG. 16 represents the proportion of seroconversion after injection of mice with vaccine grade hepatitis B surface antigen plus adjuvants. Female BALB/C mice (10 per group) were injected subcutaneously with 500 μg of standard or ultra-fine formulations of Algammulin plus 1 μg of antigen. Those sera taken after 28 days that showed an increase in specific antibody (as tested by ELISA) greater than 50% above the mean base-line for specific antibody present before injection were scored as positive seroconversions.

FIG. 16 shows a similar experiment using standard or ultra-fine formulations of Algammulin containing doses of a different preparation of hepatitis B surface antigen that, without adjuvant, will give detectable antibody in less than 10% of the mice. The ultra-fine formulations AG-43 and AG-45w gave more enhancement of the numbers showing seroconversion than did the standard formulation AG-37, or aluminium hydroxide alone.

6.4 Local Reaction

The only adverse effect found in the clinical trial of Algammulin with the papillomavirus E7 protein vaccine (Frazer, I. H. et al. (1999), in: Tindle R. W. (ed) "*Vaccines for Human Papillomavirus Infection and Anogenital Disease*", pp 91-104, R. G. Landes, New York) was a small local reaction (swelling and reddening) in some patients. The minor inflammation in one case was probably due to the antigen. The Algammulin batch used in the trial was AG-38. This is a standard formulation (median hydrated particle diameter 6-10 μm) and was administered in the highest dose practicable (25 mg subcutaneously).

Figure 17:
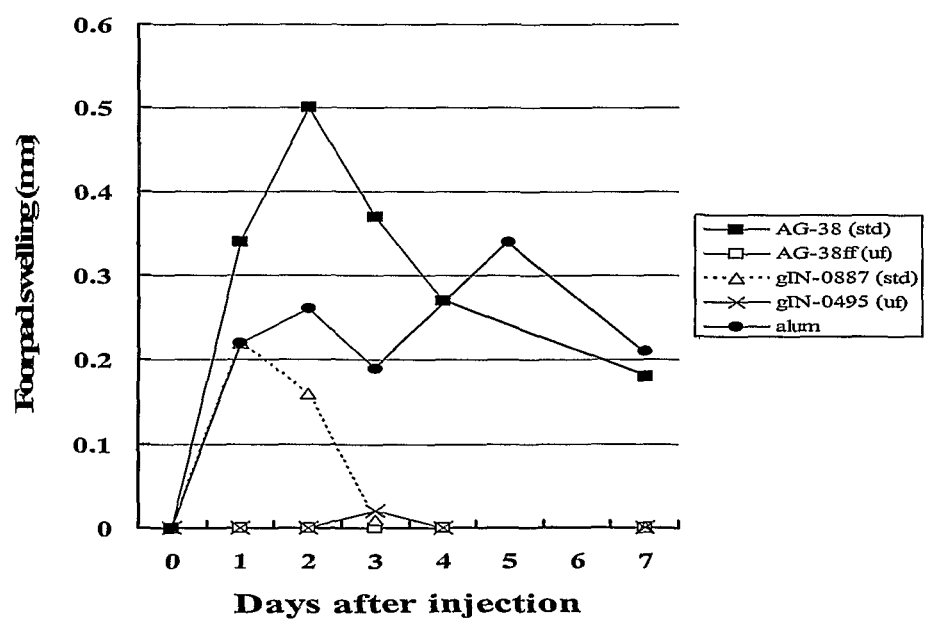
FIG. 17 shows footpad swelling after mouse plantar injection of adjuvants. Male BALB/C mice (5 per group) were injected subcutaneously into the right hind footpad with 25 μl endotoxin-free saline containing 200 μg either of standard formulations of Algammulin (AG-38) or gIN (gIN-0887), or of ultra-fine formulations of Algammulin (AG-38ff) or gIN (gIN-0495), or of aluminium hydroxide (alum), or with saline alone (left hind footpad). At intervals the difference in thickness between the hind feet of each mouse was measured with a dial gauge calliper. Results are arithmetic means of the differences.

To reduce local reaction, the methodology of the present invention was developed in part to produce inulin preparations in ultra-fine formulation (with a majority diameter 5<1 m). A reproducible skin test was also devised to assess local reaction. In this test the adjuvants were injected subcutaneously into the plantar surface of the right hand hind foot of mice and compared with the left hand hind foot injected with saline alone. A standard dose of 200 μg adjuvant per foot was selected to give maximum reaction in the most reactive component. The results show that ultra-fine formulations of Algammulin (AG-38ff) or gIN (gIN-0495) give very much less local reaction than either standard formulations (AG-38, gIN-0887) or alum (FIG. 17).

Combined use of the ultra-fine formulation and the projected normal human dose (10-20 mg subcutaneously) is expected largely to eliminate local reactions in humans.

Example 7

Discussion

The results set out in the present Examples show that delta inulin is an entity distinct from gamma inulin, and that it is useful in preparing inulin particle sizes smaller than 1 μm in diameter in a simple manner. These smaller particles have substantially enhanced ability to activate the APC. It is shown that smaller particles have other desirable properties such as lower local toxicity, greater seroconversion and emphasis of antibody types preferred for cellular immunity. In addition, the delta form itself has an adjuvant activity at least equal to that of the gamma form and an ability to activate the AP consistently greater than that of the gamma form.

Delta inulin appears to be formed from the gamma polymorph in a distinct step. Gamma conformations have only been found in higher molecular weight fractions of inulin (Cooper and Carter, 1986). The higher temperatures of complete solution of dIN compared with gIN makes it likely that its average molecular weight is higher still.

Probably inulin particles, containing a wide range of polyfructose chain lengths, comprise a loose framework only portions of which are in full crystal-like arrays. Just as some low molecular weight inulin (which on its own dissolves below 37° C.) remains co-crystallised with gIN particles created at 37° C. but can be leached out at say 45° C., so chains just long enough to assemble in the gamma conformation are leached out at typically 55° C. to leave a skeleton of longer chains in the delta conformation. Further leaching at 60° C. leaves the particles more disorganised to comprise the 'ghost' preparations described above. Their amorphous, paste-like appearance may only reflect an open, relatively non-ordered structure, a physical rather than chemical change, as the gamma and delta forms subsequently crystallised from their complete solution were indistinguishable macroscopically from the forms from which the ghosts were derived, even to their 'swirly' (anisotropic) behaviour in dilute suspension.

Progressive decreases in pellet density with gIN particle size indicated that a lower mass caused particles to swell, that is, to increase hydration. This somewhat offset the reduction in diameter, but the less than 2-fold decrease in density, that is less than 2-fold increase in volume, of the finest preparation compared with a standard formulation (gIN-1285 in Table 1) showed that the increase in diameter was only of the order of the cube root of 2 (=1.26), that is, not large. The increase in complement activation activity found with smaller particle size may be related to an increase in availability of internal inulin arrays with this increased hydration, or to an increase in surface area per unit volume.

Fine or ultra-fine formulations are also quite viscous. The lowest pellet density found was about 90 mg/ml. Since the concentration of the suspensions was 50 mg/ml, this density is approaching the limit of a solid suspension at these levels. The drop in $OD_{700}$ with particle size reflects the decrease in light scatter as the particle diameters approach the wavelength of the light used (700 nm).

Those skilled in the art will appreciate that the invention described herein is susceptible to variations and modifications other than those specifically described. It is to be understood that the invention includes all such variations and modifications.

The invention also includes all of the steps, features, compositions and compounds referred to or indicated in this specification, individually or collectively, and any and all combinations of any two or more of said steps or features.

The invention claimed is:

1. Inulin in a delta polymorphic form, wherein said inulin has a 50% optical density at 700 nanometers ($OD_{700}$) thermal transition point in dilute suspension in a temperature range of from 53° C. to 58° C.

2. The inulin according to claim 1, wherein a majority of said particles has a diameter less than 1 μm.

3. The inulin according to claim 2, wherein a majority of said particles has a diameter in a range from about 50 nm to 600 nm.

4. The inulin according to claim 1, wherein said inulin has a lower rate of solution in aqueous media than gamma inulin between 40 and 58° C.

5. The inulin according to claim 4, wherein said inulin has a lower rate of solution in aqueous media than gamins inulin between 50 and 58° C.

6. An immunological composition comprising the inulin according to claim 1 together with a pharmaceutically acceptable carrier, diluent or excipient.

7. An immunological composition comprising the inulin according to claim 1 together with an antigen-binding carrier material.

8. The composition according to claim 7, wherein said antigen-binding carrier material comprises at least one of aluminium hydroxide gel, calcium phosphate gel or aluminium phosphate gel.

9. The composition according to claim 1 together with an antigen.

10. A composition comprising inulin wherein greater than 40% of the inulin is the inulin of claim 1.

11. A composition comprising inulin wherein greater than 85% of the inulin is the inulin of claim 1.

12. The inulin of claim 1, wherein said dilute suspension is a dilute suspension of inulin present at a concentration of 0.5 mg/ml.

13. A method for the preparation of delta inulin, wherein said delta inulin has a 50% OD700 thermal transition point in dilute suspensions of from 53° C. to 58° C., comprising heating a concentrated aqueous suspension comprising 10 mg/ml or greater gamma inulin, wherein said gamma inulin has a 50% OD700 thermal transition point in dilute aqueous suspensions less than 53° C., at a temperature of 50° C. to 70° C. for a time of from 30 minutes to 10 hours.

14. The method according to claim 13, wherein said temperature is greater than 55° C. and said time is in a range of from about 30 minutes to 3 hours.

15. The method according to claim 13, wherein said temperature is about 56° C. and said time is in a range of from about 30 minutes to 3 hours.

16. The method according to claim 13, wherein said temperature is about 57° C. and said time is in a range of from about 30 minutes to 3 hours.

17. The method according to claim 13, wherein said temperature is about 58° C. and said time is in a range of from about 30 minutes to 3 hours.

18. The method according to claim 13, wherein said temperature is about 59° C. and said time is in a range of from about 30 minutes to 3 hours.

19. The method according to claim 13, whereby at the completion of the steps detailed in claim 13, the delta inulin suspension is then heated at a temperature in a range of from 60° C. to 70° C. for a time of up to 1 hour.

20. The method according to claim 13, wherein said suspension further comprises a pharmaceutically acceptable carrier, diluent or excipient.

21. The method according to claim 13, wherein said suspension further comprises an antigen-binding carrier material.

22. The method according to claim 21, wherein said antigen-binding carrier material comprises at least one of aluminium hydroxide gel, calcium phosphate gel or aluminium phosphate gel.

23. Delta inulin prepared in accordance with the method of claim 13, wherein said delta inulin has a 50% OD700 thermal transition point in dilute suspensions of from 53° C. to 58° C.

24. An immunological composition comprising the inulin according to claim 23 together with a pharmaceutically acceptable carrier, diluent or excipient.

25. An immunological composition comprising the inulin according to claim 23 together with an antigen-binding carrier material.

26. The composition according to claim 25, wherein said antigen-binding carrier material comprises at least one of aluminium hydroxide gel, calcium phosphate gel or aluminium phosphate gel.

27. A method for stimulating an immune response comprising administering to a subject an effective amount of an immunotherapeutic agent comprising the inulin according to any one of claim 1 or 23.

28. The method according to claim 27, wherein said immune response comprises activation of the alternative pathway of complement.

29. A method for enhancing an immune response comprising administering to a subject an effective amount of an adjuvant comprising the inulin according to any one of claim 1 or 23.

* * * * *